United States Patent
Yachin

(10) Patent No.: US 10,603,561 B2
(45) Date of Patent: Mar. 31, 2020

(54) PHYSICAL TRAINING SYSTEM AND METHODS USEFUL IN CONJUNCTION THEREWITH

(71) Applicant: LUDUS MATERIALS LTD., Gderot (IL)

(72) Inventor: Nir Yachin, Gderot (IL)

(73) Assignee: LUDUS MATERIALS LTD., Gderot (IL)

( * ) Notice: Subject to any disclaimer, the term of this patent is extended or adjusted under 35 U.S.C. 154(b) by 525 days.

(21) Appl. No.: 15/316,168

(22) PCT Filed: Jun. 4, 2015

(86) PCT No.: PCT/IL2015/050571
§ 371 (c)(1),
(2) Date: Dec. 4, 2016

(87) PCT Pub. No.: WO2015/186132
PCT Pub. Date: Dec. 10, 2015

(65) Prior Publication Data
US 2017/0319931 A1   Nov. 9, 2017

Related U.S. Application Data

(60) Provisional application No. 62/008,027, filed on Jun. 5, 2014, provisional application No. 62/089,361, filed on Dec. 9, 2014.

(51) Int. Cl.
*G09B 19/00* (2006.01)
*A63B 69/00* (2006.01)
(Continued)

(52) U.S. Cl.
CPC ........ *A63B 69/004* (2013.01); *G09B 19/0038* (2013.01); *A63B 69/32* (2013.01); *A63B 2024/0037* (2013.01)

(58) Field of Classification Search
USPC ......................................................... 434/247
See application file for complete search history.

(56) References Cited

U.S. PATENT DOCUMENTS 7,402,743 B2 * 7/2008 Clark .................. G10H 1/0008
250/206
9,579,048 B2 * 2/2017 Rayner ................ A61B 5/1118
(Continued)

FOREIGN PATENT DOCUMENTS

KR       20-0245616       10/2001
KR       20130000922      2/2013
(Continued)

*Primary Examiner* — Kesha Frisby
(74) *Attorney, Agent, or Firm* — JMB Davis Ben-David

(57) ABSTRACT

A physical activity training system operative in conjunction with at least one physical target with which the trainee is expected to interact in trainee activity modes, the system comprising sensor module/s operative to execute real-time measurements of aspect/s of the trainee's interaction with the target, without imaging the trainee; and an output generator including indicator/s operative to enter selectable trainee-detectable states each for a respective time period, thereby to indicate to the trainee which of the trainee activity modes governs (e.g. is in effect) within each time period, and a processor operative to monitor at least one trainee's interaction with the target within the modes, at least by generating, for storage in computer memory, time-stamped records of the modes or states and associated with the records, trainee scores derivable from the measurements generated by the module.

16 Claims, 19 Drawing Sheets

(51) Int. Cl.
  *A63B 69/32* (2006.01)
  *A63B 24/00* (2006.01)

(56) References Cited

U.S. PATENT DOCUMENTS

| | | | |
|---|---|---|---|
| 2011/0021326 A1* | 1/2011 | Oh | A63B 69/004 |
| | | | 482/84 |
| 2012/0108394 A1 | 5/2012 | Jones et al. | |
| 2012/0206330 A1* | 8/2012 | Cao | G06F 3/0383 |
| | | | 345/156 |
| 2012/0238407 A1 | 9/2012 | Dilworth et al. | |
| 2013/0302768 A1 | 11/2013 | Webb | |

FOREIGN PATENT DOCUMENTS

| | | |
|---|---|---|
| WO | 2006099320 | 9/2006 |
| WO | 2012/024060 | 2/2012 |

* cited by examiner

Fig. 4

| ID | Characteristic |
|---|---|
| FREQ_001_001 | The system may enter single strike mode after pressing on one of the green buttons (left\right green button). |
| FREQ_001_002 | The system may wait for 500ms before turning on the indication. |
| FREQ_001_003 | The system may turn on green LED respectively to the button pressed and white LED at the opposite. |
| FREQ_001_004 | The LED may be turned on for 500ms. |
| FREQ_001_005 | The system may start counting time to strike until strike retrieved or interval of 3 Seconds ends. |
| FREQ_001_006 | The system may change the mode display. |
| FREQ_001_007 | The system may interrupted by tact switch or accelerometer . |
| FREQ_001_008 | After interrupt:<br>• The system may retrieve the last altitude (or average) .<br>• The system may stop the counter. |
| FREQ_001_009 | The system may update the display with the result of the last strike (Response time, Altitude). |

Fig. 5

| ID | Characteristic |
|---|---|
| FREQ_002_001 | The system may enter fake strike mode after pressing on one of the yellow buttons (left\right yellow button). |
| FREQ_002_002 | The system may wait for 500ms before turning on the indication. |
| FREQ_002_003 | The LED may be turned on for 500ms. |
| FREQ_002_004 | The system may turn on yellow LED respectively to the button pressed and white LED at the opposite. |
| FREQ_002_005 | The system may change the mode display. |

Fig. 6a

| ID | Characteristic |
|---|---|
| FREQ_003_001 | The system may enter multiple strike mode after pressing on the purple button. |
| FREQ_003_002 | The system may wait 2 Seconds for multiple clicks on the purple button. Each click increments to section timer with 15 additional seconds. |
| FREQ_003_004 | The system may turn on purple LED on both sides for 500ms. |
| FREQ_003_005 | The system may change the mode display. |
| FREQ_003_006 | The system may disable the other modes buttons. |
| FREQ_003_007 | The system may start counting time. |
| FREQ_003_008 | The system may increment strikes counter after each impact switch interrupt (strike). |
| FREQ_003_009 | The system may interrupt by holding the purple button for 2 seconds and aborting the section. |
| FREQ_003_010 | The system may blink the Purple LED in the last 10 seconds. Blinking ratio of 50% turned off\on. |
| FREQ_003_011 | The system may update the display with the result of the last strike.<br>(total time ‖ total strikes) |

Fig. 6b

| ID | Characteristic |
|---|---|
| FREQ_004_001 | The system may measure the altitude. |
| FREQ_004_002 | The measurement may be made by one of the two options each of which may include some or all of the following steps :<br>• Step1: Enabling the altitude sensor.<br>　Step2: Start counting time.<br>　Step3: The system interrupted by the sensor.<br>　Step4: Stop counting.<br>　Step5: Convert the counted time to height result.<br>• Step1: Enabling the altitude sensor. The system waits for digital returned result. Step2: Returned result is converted to height. |

PHYSICAL TRAINING SYSTEM AND METHODS USEFUL IN CONJUNCTION THEREWITH

REFERENCE TO CO-PENDING APPLICATIONS

This is the U.S. National Stage of International Application No. PCT/IL2015/050571, filed Jun. 4, 2015, which was published in English under PCT Article 21(2), which in turn claims the benefit of United States Provisional Patent Application No. 62/008,027 filed on Jun. 5, 2014 and entitled "Martial Arts Training System Particularly Suited To Group Instruction And/Or Eradication Of Impulsive Responses And/Or Development Of Skills Targeting Plural Body Heights" and from United States Provisional Patent Application No. 62/089,361, entitled "Physical training systems and methods suitable for taekwondo and other uses" and filed Dec. 9, 2014.

FIELD OF THIS DISCLOSURE

The present invention relates generally to a physical training apparatus and more particularly to a computerized physical training apparatus.

BACKGROUND FOR THIS DISCLOSURE

The disclosures of all publications and patent documents mentioned in the specification, and of the publications and patent documents cited therein directly or indirectly, are hereby incorporated by reference. Materiality of such publications and patent documents to patentability is not conceded.

SUMMARY OF CERTAIN EMBODIMENTS

One of the main training accessories useful e.g. in martial arts is a paddle or other target used for kicking and punching. These punches and kicks or other impacts and blows to the target are not measured by objective tools in conventional systems; instead, training relies mostly on the trainer's perception.

Certain embodiments seek to provide an improved physical activity training device, which may be configured as a paddle (also termed herein "beater"), ball, surface, cushion, mitt, body protector, punching bag, hugo etc. or may be multi-purpose and have an associated set of removable heads converting the multi-purpose device into a paddle, ball, surface, etc. Each such head may be associated with different signaling functionalities and different analysis of events (different states and statuses). Typically, the trainee is being trained to contact e.g. kick or strike the target a certain number of times and in certain ways (aspects such as how many times/how frequently/how accurately/how fast—response time, etc.) e.g. depending on the mode of trainee response (typically from among a "library" of pre-defined trainee response modes) which is required by a particular training program which may be used by a particular trainer, trainee or common to a (typically predefined) group of trainers/trainees.

Certain embodiments seek to provide a martial arts training system particularly suited to group instruction and/or eradication of impulsive responses and/or development of skills targeting plural body heights.

Any suitable technology may be provided to measure and record target height relative to a reference height such as the floor, at the time of contact of the trainee with the device, such as but not limited to laser/ultrasound/sonar/accelerometer technologies or any combination thereof.

It is appreciated that signals to the trainee need not be lights of specific colors; other colors may be employed or lights may be replaced by sounds or any other trainee-sensitive signal. The device shown herein is not limited in its applicability to Taekwondo in particular or even to the martial arts and instead is suited for monitoring and improving the quality of a wide variety of physical activities.

Contact with the device by the trainee may be made by kicking the device or by any other means e.g. handshaking the device.

Distances (e.g. between the device herein and an accessory co-located with the trainee such as a glove, sock, bracelet or chest-shield), may be measured for a situation ("Situation 2" or "signal 2") in which a green light signals to the trainee to kick once and as fast as possible. It is appreciated, however, that distance measurement may occur at any suitable time and using any suitable distance measurement technique depending on the ability of the accessory, if any, to cooperate with the device herein to yield a distance measurement between them. For example, the device, depending e.g. on the above circumstances, may or may not include "situation 2" above and may or may not include a situation in which a purple light is employed to signal to the trainee to kick as many times as s/he can. Obviously, the particular use of certain colors in this description and these drawings is not intended to be limiting.

Complex signals may be employed e.g. a fixed light may begin to flash; one light may be combined with another or with a sound. Each signal may denote any suitable activity such as "stop handshakes until the light turns back off", "reduce your pace/rhythm in order to move from aerobic activity to anaerobic activity", "do not kick while this signal is in force", etc.

Similar signals which are difficult to distinguish from one another, such as similar colors, may be employed to denote situations which are difficult to distinguish in real life. For example, if it is difficult to distinguish, in Taekwondo, situations which mandate a kick from "fake" situations which do not, similar colors such as green and almost-green may be employed to denote "kick once" and "do not kick while this signal is in force", respectively.

For example, signals or modes may include some or all of the following:
1. Don't kick
2. Kick once as fast as you can, responsive to a certain stimulus "2"
3. Fake—don't kick
4. Sequence which does not resemble signals 2, 3 above—kick as fast as you can when sequence concludes
5. Multipule
6. Kick as fast as you can, responsive to stimulus which differs from stimulus "2" above The following statuses may be reported when a handshake (e.g. trainee-target contact) is identified during each of the above signals or modes respectively:
1. Off handshake
2. Good
3. Wrong
4. Wrong flash state
5. Status to depend on precise combination of lights or signals
6. Good Embodiments include but are not limited to:
EMBODIMENT A: A physical activity training device providing signals indicating which of several trainee activity modes are appropriate at given times; and/or providing real-time measured feedback re quality of a trainee's activity without imaging the trainee.

EMBODIMENT B: A device which is configured as one of: a paddle, ball, surface.

EMBODIMENT C: A device which is multi-purpose and has an associated set of removable heads converting the multi-purpose device into selectable configurations such as but not limited to any of: a paddle, ball, surface, etc.

EMBODIMENT D: A device wherein each such head is associated with different signaling functionalities and different analysis of events (different states and statuses).

EMBODIMENT E: A device wherein distances are measured between the device and a cooperating accessory co-located with the trainee.

EMBODIMENT F: A device wherein said accessory comprises any one of: a glove, sock, bracelet or chest-shield.

EMBODIMENT G. A device wherein said device has personalization functionality.

EMBODIMENT H. A device wherein said device has distance measurement functionality.

EMBODIMENT I. A device wherein said device has a programmable indicator having at least 2 states.

EMBODIMENT J. A device wherein said device has functionality for measuring height.

EMBODIMENT K. A device wherein said device has control functionality operative to train trainees to achieve each of a plurality of martial arts skills at each of at least 2 heights (e.g. body, head).

EMBODIMENT L. A training system comprising:
    A complementary device having:
        at least one of personalization functionality and distance measurement functionality; and
        a programmable indicator having at least 2 states.

EMBODIMENT M. A martial arts training system comprising:
    Functionality for measuring height; and
    control functionality operative to train trainees to achieve each of a plurality of martial arts skills at each of at least 2 heights (body, head).

EMBODIMENT N. A system wherein a body guard that functions as a scoring target, e.g. hogu, is used to indicate whether a martial arts attack has achieved body height.

EMBODIMENT P. At least one processor configured to perform at least one of or any combination of the described steps or to execute any combination of the described modules.

Abbreviations employed include:
LCD Liquid Crystal Display
LED Light Emitting Diode
A\D Analog to Digital
FW Firmware
SPI Serial Peripheral Interface
GPIO General purpose Input Output
BAT. Battery
St. Status
IEV or LEV Level
IDC Internet Direct Connection
USB Universal Serial Bus
ADC Analog-to-digital converter
JTAG Joint Test Action Group testing of finished e.g. in-system programming (ISP) printed circuit boards The scope of the present invention also includes at least the following embodiments:

Embodiment 1: A physical activity training system operative in conjunction with at least one physical target with which the trainee is expected to interact in each of a plurality of trainee activity modes, the system comprising:
    at least one sensor module operative to execute real-time measurements of at least one aspect of the trainee's interaction with the target, without imaging the trainee; and
    an output generator including at least one indicator operative to enter a plurality of selectable trainee-detectable states each for a respective time period, thereby to indicate to the trainee which of the plurality of trainee activity modes governs (e.g. is in effect) within each said time period, and
    a processor operative to monitor at least one trainee's interaction with the target within the modes, at least by generating, for storage in computer memory, time-stamped records of said states and associated with said records, trainee scores derivable from said measurements generated by said module.

The trainee may be trained for any sport including ball games, athletics, and martial arts training such as but not limited to taekwondo, judo, krav maga and karate; or for physiotherapy operations prescribed by a physiotherapist.

The target may comprise any or all of: a paddle/mitt/cushion/punching bag/ball/surface; or a personalized device storing data about a single trainee; or a group-specific device storing data about a single group.

The target may be multi-purpose e.g. may have an associated set of removable heads converting the multi-purpose target into selectable configurations such as but not limited to any of: a paddle, ball, surface, etc. Each such head may be associated with different signaling functionalities and/or different analyses of events and/or different states and/or different statuses.

The trainee scores may be the raw measurements themselves or various sophisticated, often mode-specific quantifications computed by the processor such as, for example, number of blows to the target within a time window, distance, height, blow velocity measurement quantifying the instantaneous speed of a trainee's blow when the trainee contacts the target, and so forth.

The processor may communicate with and control the output generator including commanding the output generator as to when to enter each of the plurality of selectable trainee-detectable states, typically corresponding to a plurality of selectable trainee activity modes; the trainee is expected to train—e.g. by interacting with the target—in according with these modes.

Example: According to certain embodiments, when "single" mode is entered, the trainee is expected to kick a selectable one of the surfaces e.g. a left/right/top/bottom surface of the target of FIGS. 19a-19d, once, as fast as possible. The processor may command the output generator to illuminate the LED of (say) the left surface in a first color (green, say) and the LED of another surface (say the right surface), in a second color (white, say). In this example, if the selectable surface is the right rather than left surface, the colors of the 2 LEDs may be reversed.

Embodiment 2: A physical activity training system according to any of the preceding claims and also comprising a processor operative to use a mode-specific process to derive, at least partly from least one real-time measurement, at least one score characterizing the trainee's performance within an individual mode from among the plurality of trainee activity modes.

The score may include an indication of the time that elapsed from when the indicator of an individual mode was displayed, to the time at which the trainee first interacted with the target in a manner which complies with said individual mode.

In "single" mode, the mode specific process may compute, and the score may comprises an indication of, how fast (time of impact with target minus time that "single" mode indicator was displayed) and/or how hard the trainee kicked the target e.g. based on data from suitable sensors which may be mounted in the target.

In "multiple" mode, the mode specific process may compute, and the score may reflect, inter alia, how many times the trainee kicked and how hard the trainee kicked on average. Generally, the system computes pre-defined situational and/or outcome data characterizing the trainee's activities within each mode. In "multiple" mode or state the system may compute all variables computed in single mode. Moreover the multiple mode may be employed to present stamina related characterizations of the trainee's activities such as a graph that illustrates changes in the blow (kick, punch or other impact) status such as but not limited to the blow's strength\speed\accuracy.

Embodiment 3. A physical activity training system according to any of the preceding claims wherein the indicator simulates an actual occurrence which, in an actual competitive and/or training event, signals to trainee which of the plurality of trainee activity modes governs at a current time.

According to certain embodiments, a processor may directly or via a local processor communicate with and control the output generator from afar; for example, a central computer controlling trainee activity modes may even be located in another country.

For example, if the occurrence signaling to trainee that the event has begun is audio, at least one indicator used by the output generator to indicate a trainee activity mode useful at the moment an event begins, may be audio.

For example, if the occurrence signaling to a trainee during an actual competitive event that a particular mode is to be employed, is a visually sensible occurrence such as an opponent's punch or kick, at least one indicator used by the output generator to indicate that particular mode, may be visual such as a light.

For example, if the occurrence signaling to a trainee during an actual competitive event that a particular mode is to be employed, is laterally specific (a visually or otherwise sensible occurrence which is seen on or heard from the right or from the left), at least one indicator used by the output generator to indicate that particular mode, may be laterally specific. For example, a pair of visual indicators positioned respectively on the right and left sides of the trainee may be used to indicate to the trainee that a laterally-specific mode of activity is now appropriate. For example, a right-hand light may turn on to indicate a mode in which the trainee defends himself from an opponent's kick from the right whereas a left-hand light may turn on to indicate a mode in which the trainee defends himself from an opponent's kick from the left.

An advantage of certain embodiments is that the physical components/hardware may be very generic (may not be specific to only one sport or only one level of or type of training) and may nonetheless be useful in training an athlete to engage in a wide variety of sports (such as martial, athletics, ball-games, team sports), at a wide variety of levels, using a wide variety of training types and techniques.

Embodiment 4. A physical activity training system according to any of the preceding claims wherein in at least one of the modes the trainee is expected to refrain from a certain category of interactions with the target and wherein said trainee scores indicate whether or not the trainee has refrained from said category of interactions.

For example, in a "fake kick" mode, the trainee may be expected to refrain from any (all) interactions with the target and the trainee scores may indicate whether or not the trainee interacted with the target while "fake kick" mode was in effect.

More generally, it is appreciated that "fake" mode referred to throughout is merely an example of a mode in which the trainee is expected to refrain from at least one activity; while these modes govern, the system typically records each instance in which the trainee (inappropriately) engaged in this activity. In martial arts for example, training to refrain from certain activities, sometimes close to instinctive, which under certain circumstances could allow the opponent to launch an attack, is thereby facilitated. Such circumstances include for example a rapid "faking" move by the opponent designed to elicit a certain activity which leaves the body unprotected thereby enabling the opponent to attack successfully.

Embodiment 5. A system according to any of the preceding embodiments wherein an indicator for at least one mode (state) in which interaction with the target is expected comprises a light having a first color and wherein the indicator for at least one "refrain" mode in which said interaction with the target is prohibited comprises the same light but having a second color different from the first color.

Embodiment 6. A system according to any of the preceding embodiments and wherein, in at least one mode from among the plurality of trainee activity modes, the mode specific process may compute, and the score may reflect, how hard the trainee struck (e.g. kicked) the target.

During certain modes, any suitable computational or logical combination of parameters may be sensed and/or computed such as instances of soft rapid blows vs. instances of hard slow blows.

Embodiment 7. A system according to any of the preceding embodiments and wherein said output generator is operative to indicate which mode governs by providing an indication sensible by the trainee when s/he is within normal training distance from the target.

For example, a visual or audio indication such as an illuminated LED might be provided which is visible to or audible by the trainee when the target-trainee distance is whatever is appropriate for a particular sport or game or other activity being learned by the trainee.)

Embodiment 8. A system according to any preceding claim wherein said memory also stores at least one estimation of trainee-target distance.

Embodiment 9. A system according to any of the preceding embodiments wherein the memory stores a sequence of time-stamped estimations of trainee-target distance respectively associated with the time-stamped records of said states and trainee scores.

Embodiment 10. A system according to any preceding claim wherein said memory also stores at least one estimation of target height relative to a reference level.

Control functionality, operative to train trainees to achieve each of a plurality of martial arts skills at each of at least 2 heights (body, head), may be provided e.g. for Taekwondo.

Height may be measured relative to a system-defined or user-defined reference or zero height. For example, a trainee activity recording device, such as any shown and described herein, may be provided which has a selectable calibration mode enabling a specific zero height to be defined at will;

trainee activities may then be defined relative to that height and the trainee's performance in executing these activities may be recorded.

For example, the system may be programmed to record the number of times the trainee managed to kick the target when it is 30-50 cm higher than a particular zero-height just calibrated; and may also record how hard each such kick was. The trainee may also be expected to refrain from kicking the target when it is less then 30 cm, or more than 50 cm, higher than the zero-height.

The target may comprise a body-guarding substrate mounted at a specific height on the body of an individual such as the trainer or held freely by the trainer. e.g. a hogu, and may be used to indicate whether a martial arts attack has achieved that specific height; for example a sound wave may be emitted (e.g. by an ultrasound cone such as that shown in FIG. 19b) from the target to the floor (i.e., throughout the specification, relative to a system-defined or user-calibrated reference height such as but not limited to floor height). The time required for the wave to return to the target/cone may be measured and used to deduce the height of the target vis a vis (say) the floor.

A particular advantage of certain embodiments is that a trainer can program the system using a suitable user interface, or the system may be pre-programmed, to record trainee activity separately for each of several target heights. For example, a trainer might discover that a particular trainee's blows are neither hard enough nor fast enough, for heights exceeding 170 cm, whereas the same trainee's blows are recorded as satisfying pre-stored norms, in terms of both intensity and speed, for all heights up to 170 cm.

Embodiment 11. A system according to any of the preceding embodiments wherein the memory stores a sequence of time-stamped estimations of target height respectively associated with the time-stamped records of said states and trainee scores.

Embodiment 12. A system according to any preceding claim and wherein at least one of the sensor module and the output generator are programmable via a user interface.

The user interface may be disposed at a remote location and be operative to communicate e.g. wirelessly or via a wired connection with the target or may be mounted on the target.

Embodiment 13. A system according to any preceding claim and also comprising an interface of the target with an on-line database which generates comparisons between a trainee's records in the memory and a norm stored in the database which is updated in real time.

Embodiment 14. A system according to any preceding claim and also comprising an interface between the target and a mobile device which enables data about the trainee to be transferred from memory to the mobile device after a training session and from mobile device to memory before a session.

Embodiment 15. A system according to any of the preceding embodiments wherein said mobile device comprises a mobile communication device.

For example, the target may communicate via Bluetooth to any of the following mobile communication devices:
  a. PC
  b. Laptop
  c. Tablet
  d. mobile/Cell phone e.g. smartphone Embodiment 16. A system according to any of the preceding embodiments wherein said estimation is generated based at least partly on a measurement of distance between the device and a cooperating accessory co-located with the trainee.

The accessory may for example comprise any of: a glove, sock, bracelet or chest-shield or other article which may be worn by or affixed to the trainee. Laser measurements may optionally be used for the distance measurement. Any suitable technology may be employed such as but not limited to triangulation if 3 cooperating locations are available e.g. trainer, trainee, other; measuring power drop from a source of known power; and measuring travel time for a signal of known velocity.

Embodiment 17. A physical activity training system according to any of the preceding embodiments wherein the indication is mounted on the target.

Embodiment 18. A physical activity training method operative in conjunction with at least one physical target with which the trainee is expected to interact in each of a plurality of trainee activity modes, the method comprising:

Using at least one sensor module to execute real-time measurements of at least one aspect of the trainee's interaction with the target, without imaging the trainee; and Using an output generator including at least one indicator to enter a plurality of selectable trainee-detectable states each for a respective time period, thereby to indicate to the trainee which of the plurality of trainee activity modes governs within each said time period, and Using a processor to monitor at least one trainee's interaction with the target within the modes, at least by generating, for storage in computer memory, time-stamped records of said states and associated with said records, trainee scores derivable from said measurements generated by said module.

Embodiment 19. A computer program product, comprising a non-transitory tangible computer readable medium having computer readable program code embodied therein, said computer readable program code adapted to be executed to implement a physical activity training method operative in conjunction with at least one physical target with which the trainee is expected to interact in each of a plurality of trainee activity modes, said method comprising the following operations:

Using output from at least one sensor module to generate real-time measurements of at least one aspect of the trainee's interaction with the target, without imaging the trainee;

Using an output generator including at least one indicator to enter a plurality of selectable trainee-detectable states each for a respective time period, thereby to indicate to the trainee which of the plurality of trainee activity modes governs within each said time period, and Using a processor to monitor at least one trainee's interaction with the target within the modes, at least by generating, for storage in computer memory, time-stamped records of said states and associated with said records, trainee scores derivable from said measurements generated by said module.

Also provided, excluding signals, is a computer program comprising computer program code means for performing any of the methods shown and described herein when said program is run on at least one computer; and a computer program product, comprising a typically non-transitory computer-usable or -readable medium e.g. non-transitory computer-usable or -readable storage medium, typically tangible, having a computer readable program code embodied therein, said computer readable program code adapted to be executed to implement any or all of the methods shown and described herein. The operations in accordance with the teachings herein may be performed by at least one computer specially constructed for the desired purposes or general purpose computer specially configured for the desired purpose by at least one computer program stored in a typically non-transitory computer readable storage medium. The term "non-transitory" is used herein to exclude transitory, propagating signals or waves, but to otherwise include any volatile or non-volatile computer memory technology suitable to the application.

Any suitable processor/s, display and input means may be used to process, display e.g. on a computer screen or other computer output device, store, and accept information such as information used by or generated by any of the methods and apparatus shown and described herein; the above processor/s, display and input means including computer programs, in accordance with some or all of the embodiments of the present invention. Any or all functionalities of the invention shown and described herein, such as but not limited to operations within flowcharts, may be performed by any one or more of: at least one conventional personal computer processor, workstation or other programmable device or computer or electronic computing device or processor, either general-purpose or specifically constructed, used for processing; a computer display screen and/or printer and/or speaker for displaying; machine-readable memory such as optical disks, CDROMs, DVDs, BluRays, magnetic-optical discs or other discs; RAMs, ROMs, EPROMs, EEPROMs, magnetic or optical or other cards, for storing, and keyboard or mouse for accepting. Modules shown and described herein may include any one or combination or plurality of: a server, a data processor, a memory/computer storage, a communication interface, a computer program stored in memory/computer storage.

The term "process" as used above is intended to include any type of computation or manipulation or transformation of data represented as physical, e.g. electronic, phenomena which may occur or reside e.g. within registers and/or memories of at least one computer or processor. The term processor includes a single processing unit or a plurality of distributed or remote such units.

The above devices may communicate via any conventional wired or wireless digital communication means, e.g. via a wired or cellular telephone network or a computer network such as the Internet.

The apparatus of the present invention may include, according to certain embodiments of the invention, machine readable memory containing or otherwise storing a program of instructions which, when executed by the machine, implements some or all of the apparatus, methods, features and functionalities of the invention shown and described herein. Alternatively or in addition, the apparatus of the present invention may include, according to certain embodiments of the invention, a program as above which may be written in any conventional programming language, and optionally a machine for executing the program such as but not limited to a general purpose computer which may optionally be configured or activated in accordance with the teachings of the present invention. Any of the teachings incorporated herein may, wherever suitable, operate on signals representative of physical objects or substances.

The embodiments referred to above, and other embodiments, are described in detail in the next section.

Any trademark occurring in the text or drawings is the property of its owner and occurs herein merely to explain or illustrate one example of how an embodiment of the invention may be implemented.

Unless specifically stated otherwise, as apparent from the following discussions, it is appreciated that throughout the specification discussions, utilizing terms such as, "processing", "computing", "estimating", "selecting", "ranking", "grading", "calculating", "determining", "generating", "reassessing", "classifying", "generating", "producing", "stereo-matching", "registering", "detecting", "associating", "superimposing", "obtaining" or the like, refer to the action and/or processes of at least one computer/s or computing system/s, or processor/s or similar electronic computing device/s, that manipulate and/or transform data represented as physical, such as electronic, quantities within the computing system's registers and/or memories, into other data similarly represented as physical quantities within the computing system's memories, registers or other such information storage, transmission or display devices. The term "computer" should be broadly construed to cover any kind of electronic device with data processing capabilities, including, by way of non-limiting example, personal computers, servers, computing system, communication devices, processors (e.g. digital signal processor (DSP), microcontrollers, field programmable gate array (FPGA), application specific integrated circuit (ASIC), etc.) and other electronic computing devices.

The present invention may be described, merely for clarity, in terms of terminology specific to particular programming languages, operating systems, browsers, system versions, individual products, and the like. It will be appreciated that this terminology is intended to convey general principles of operation clearly and briefly, by way of example, and is not intended to limit the scope of the invention to any particular programming language, operating system, browser, system version, or individual product.

Elements separately listed herein need not be distinct components and alternatively may be the same structure. A statement that an element or feature may exist is intended to include (a) embodiments in which the element or feature exists; (b) embodiments in which the element or feature does not exist; and (c) embodiments in which the element or feature exist selectably e.g. a user may configure or select whether the element or feature does or does not exist.

Any suitable input device, such as but not limited to a sensor, may be used to generate or otherwise provide information received by the apparatus and methods shown and described herein. Any suitable output device or display may be used to display or output information generated by the apparatus and methods shown and described herein. Any suitable processor/s may be employed to compute or generate information as described herein e.g. by providing one or more modules in the processor/s to perform functionalities described herein. Any suitable computerized data storage e.g. computer memory may be used to store information received by or generated by the systems shown and described herein. Functionalities shown and described herein may be divided between a server computer and a plurality of client computers. These or any other computerized components shown and described herein may communicate between themselves via a suitable computer network.

BRIEF DESCRIPTION OF THE DRAWINGS

Certain embodiments of the present invention are illustrated in the following drawings:

FIGS. 4-5, 6a-6b are tables useful in understanding certain embodiments which may for example be employed in conjunction with other embodiments illustrated herein; each table may alternatively include only some of the illustrated fields and/or records.

Figure 1:
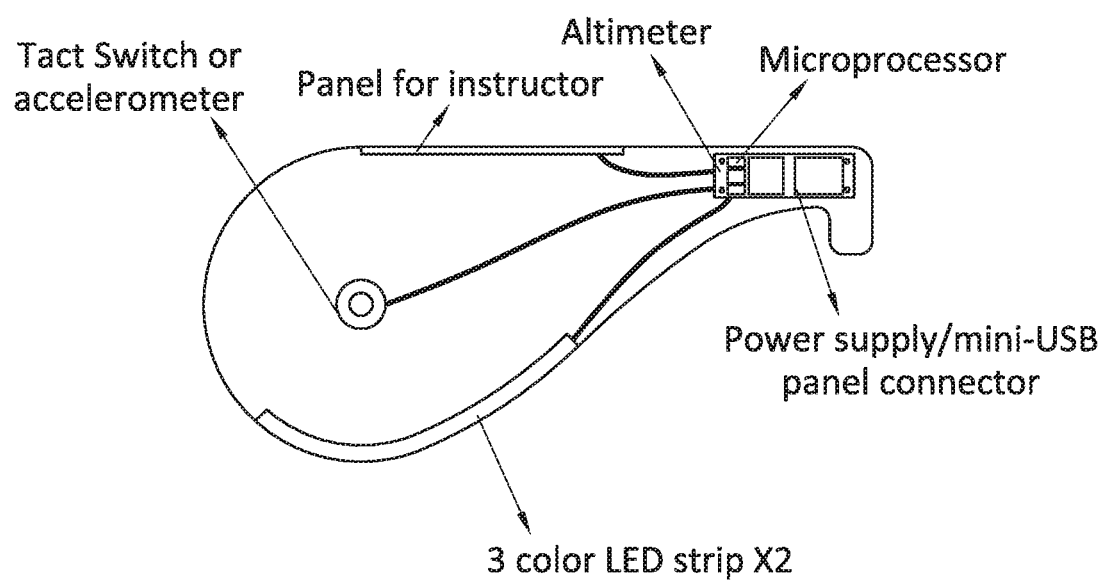
FIG. 1 shows a target apparatus constructed and operative in accordance with certain embodiments which may be employed in conjunction with other embodiments illustrated herein.

Methods and systems included in the scope of the present invention may include some (e.g. any suitable subset) or all of the functional blocks shown in the specifically illustrated implementations by way of example, in any suitable order e.g. as shown.

Computational components described and illustrated herein can be implemented in various forms, for example, as hardware circuits such as but not limited to custom VLSI circuits or gate arrays or programmable hardware devices such as but not limited to FPGAs, or as software program code stored on at least one tangible or intangible computer readable medium and executable by at least one processor, or any suitable combination thereof. A specific functional component may be formed by one particular sequence of software code, or by a plurality of such, which collectively act or behave or act as described herein with reference to the functional component in question. For example, the component may be distributed over several code sequences such as but not limited to objects, procedures, functions, routines and programs and may originate from several computer files which typically operate synergistically.

Any method described herein is intended to include within the scope of the embodiments of the present invention also any software or computer program performing some or all of the method's operations, including a mobile application, platform or operating system e.g. as stored in a medium, as well as combining the computer program with a hardware device to perform some or all of the operations of the method.

Data can be stored on one or more tangible or intangible computer readable media stored at one or more different locations, different network nodes or different storage devices at a single node or location.

It is appreciated that any computer data storage technology, including any type of storage or memory and any type of computer components and recording media that retain digital data used for computing for an interval of time, and any type of information retention technology, may be used to store the various data provided and employed herein. Suitable computer data storage or information retention apparatus may include apparatus which is primary, secondary, tertiary or off-line; which is of any type or level or amount or category of volatility, differentiation, mutability, accessibility, addressability, capacity, performance and energy use; and which is based on any suitable technologies such as semiconductor, magnetic, optical, paper and others.

DETAILED DESCRIPTION OF CERTAIN EMBODIMENTS

Certain embodiments seek to allow trainers and trainees to objectively measure several core aspects of training in order to improve the quality of the training and the progress monitor.

Some or all (any subset) of the following characteristics (a)-(h) may be provided:

a. Response time measurement: Green/Red (say) LED (say) or any other suitable indicators may turn on whenever user1 turns a switch or according to a predefined training program. User2 needs to kick/punch the target (e.g. of FIG. 1 or of FIGS. 19a-19d) as fast as he can. The paddle or target may measure the time it takes for user2 to kick/punch the paddle since the LED lit up, and may digitally store and/or show this length on a suitable display device e.g. small built-in screen. In case of no action, the paddle may show that no kick has been registered. (user1=trainer, user2=trainee).

b. Action status indicators The paddle (used in the present specification by way of example; more generally, any suitable target which is typically capable of sensing and recording trainee impact thereupon, or capable of otherwise sensing and recording parameters of trainee activity, may be employed) has some or all of the following 4 states:

State 1—Off
State 2—On—green (say)—represents a case in which user2 needs to kick exactly once, as fast as possible.
State 3—On—red (say)—Fake, don't kick: represents a fake action in which user2 should not kick e.g. since it is wiser for her or him to remain in a guarded position than it is for her/him to kick.
Stage 4—Purple (say): Kick as many times as possible.

According to certain embodiments, certain states e.g. states 2 and/or 3 may appear in combination with an indication of a direction at which to kick. For example, if 2 rows of indicators (LEDs e.g.) both light up, the direction is unimportant, whereas if only 1 row lights up, the kick should be directed at that direction (right or left e.g.).

Computerized analysis of trainee activities may include some or all of the following:

a. If the paddle identifies a kick during state 1—it registers a false kick b. If the paddle identifies a kick during state 2—it registers a positive ("good") kick c. If the paddle identifies a kick during state 3—it registers an erroneous kick d. If the paddle identifies a kick after state 2—it registers an impulsive kick.

e. If State A happens after state B and state B does not register a kick but state A does, this would be registered as a good kick, badly timed.

f. If State A happens after state B and state B does register a kick and state A does as well, the state A kick may be registered as an impulsive kick.

c. Height measurement calibration: The apparatus may be calibrated at any given time for height measurement. User1 may calibrate the height according to the actual height and may lower the paddle to the ground for "zero height" calibration, e.g. once per training session or each time it is desired to change the reference height or "zero height". Typically, the apparatus allows to register any height as the "zero height". This is advantageous because training tasks or modes may then be defined such as, say "try to kick 30 centimeters above the waist line", if the waist-line has been defined as zero height. The device may register the height upon every kick.

d. Complementary device data management abilities: A device may be attached to the trainee's clothing or body and may store in computer memory, a unique ID of the user2. User1 may insert user2's details (name, height, unique id, training programs) via an application. The data may stream to the paddle.

After every kick, the device may send the data to the paddle with user2's unique id.

Typically, the chip does not save the paddle data; instead, the chip provides the paddle with trainee ID information; the paddle may provide the data to a suitable computerized application for processing.

It is appreciated that the trainer may use the computerized application in order to remotely control state activation (of selected ones of states 1-4 e.g.).

e. Distance: The paddle may register the distance between itself and the complementary device in the following scenarios:

Every time it goes to state 2 (in the millisecond the LED turned green).

On demand f. Connectivity: The paddle can connect via Bluetooth (say) to some or all of the following devices: PC, Laptop, Tablet, cellphone.

g. Syncing and updating: Upon connecting to one of the above devices, user 1 may be able to upload the data to an online server for future monitor and analysis.

User1 may be able to create special training programs (different sequences of the described states—see "Action status" section).

User1 may be able to browse all of his user's data in a dedicated site/app.

h. Personalization: User1 can download special training programs according to the users that come to class.

The paddle may recognize (via the complementary device) user2 and extract the right program.

The system may, alternatively or in addition, include an action carpet operative to measure the exact time that a trainee's foot left the floor and subtract that time from the trainee's overall reaction time in order to derive and store data regarding the speed of the trainee's kick.

It is appreciated that the applications of the functionalities shown and described herein are not limited to Taekwondo and can include, for example, physiotherapy equipment, say for measuring functionality and recovery in post-stroke patients.

An auxiliary apparatus may be included which may interact suitably with the apparatus of the present invention, such as but not limited to a camera residing on the paddle, training cushions, punching bag, and action carpets.

According to certain embodiments, a programmable indicator is used to teach trainees to avoid impulsive responses to fake kicks. While a first state of the indicator is on, the trainee may be instructed to refrain from responding to the kick, corresponding to an initial stage of a fake kick which is impossible to distinguish from a real kick. Only once the indicator has reverted to a second state, corresponding to a later stage of a fake kick which is possible to distinguish from a real kick, is the trainee, according to instruction, to respond to the kick, if real, or to continue to refrain from responding to the kick, if the kick is fake. Typically, the indicator may have at least 3 possible states: the first state, which is followed by one of 2 states 2a and 2b, where 2a corresponds to an opponent's seeming kick which has disambiguated into a fake kick, and 2b corresponds to an opponent's seeming kick which has disambiguated into a real kick, hence requires a response. The system preferably trains to refrain from defending against the seeming kick while the indicator is in the first state, and of course in state 2a, and/or to reduce response time to a minimum as soon as the indicator has entered state 2b. A particular advantage is that several trainees may be trained simultaneously whereas absent the functionality provided by this embodiment of the invention, a human trainer may only be able to effect this type of training for one trainee at a time.

Alternatively or in addition, control functionality is provided to train trainees to achieve each of a plurality of martial arts skills at each of at least 2 heights (body, head), including monitoring and storing progress for each of a plurality of trainees.

Certain embodiments may include a paddle and/or a complementary product—a personal, attached device.

Hardware and firmware characteristics:

It is appreciated that some of all of the characteristics may be provided and may be combined between embodiments as appropriate and that any feature implemented in hardware may be implemented in firmware and vice versa. Parameters stipulated herein are merely exemplary and may be replaced by other parameters as would be known to one ordinarily skilled in the art.

Hardware characteristics, some or all of which may be provided, are now described, e.g. with reference to FIG. 1 which illustrates an example target device. Various views of an alternative embodiment are shown in FIGS. 19a-19d.

The apparatus typically includes a paddle or other target that comprises some or all of several elements operative to measure response during training.

The target may have a switch to identify a hit, height sensor, LED, LCD and control buttons. It is appreciated that alternatively to, or in addition to LEDs, any other indicator/s may be employed which may have their own trainee-detectable states rather than, or in addition to, light on/off such as audio states; blinking/steady, color, tactile states, and so forth.

Figure 3:
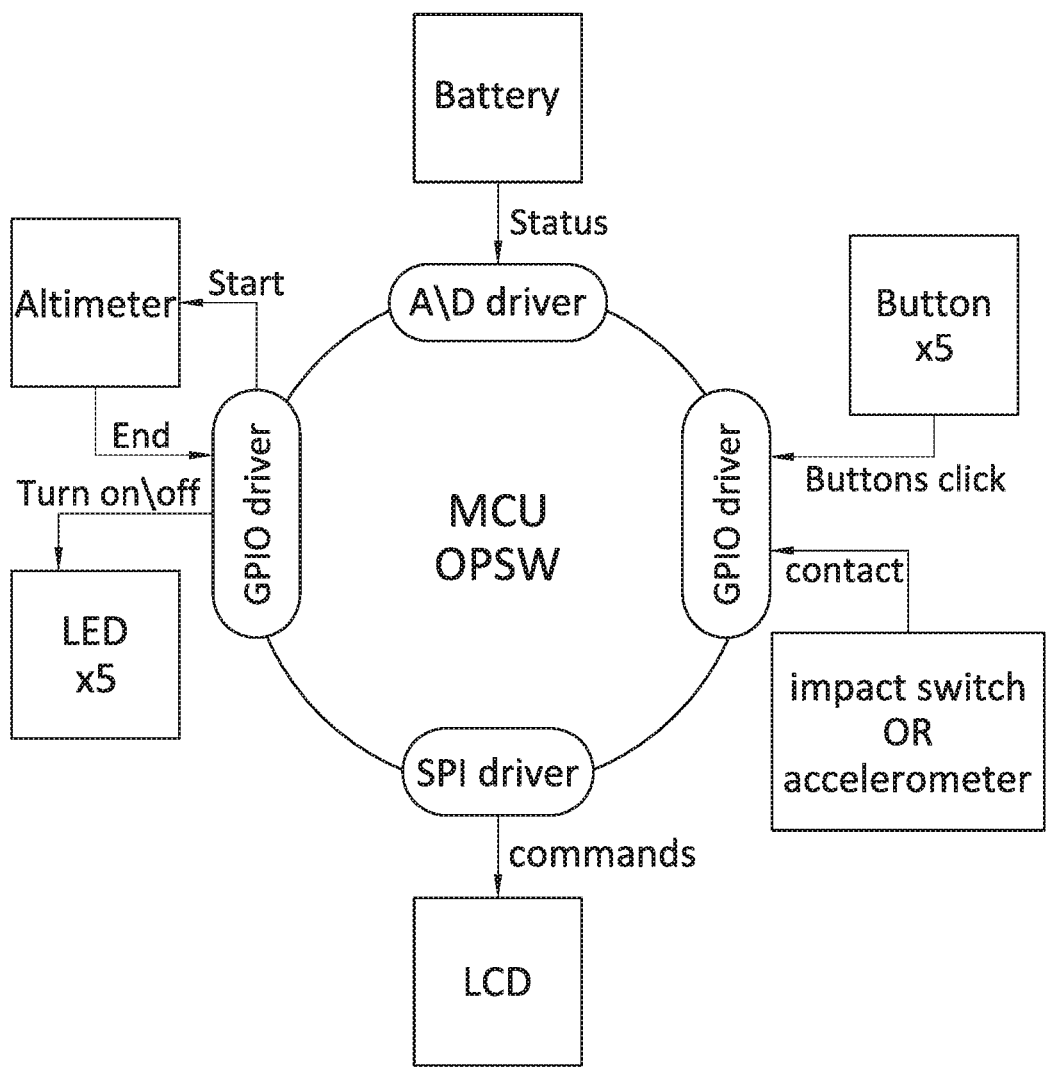

FIG. 3 is a firmware block diagram; it is appreciated that any subset of or all of the illustrated blocks may be provided.

Figure 2:
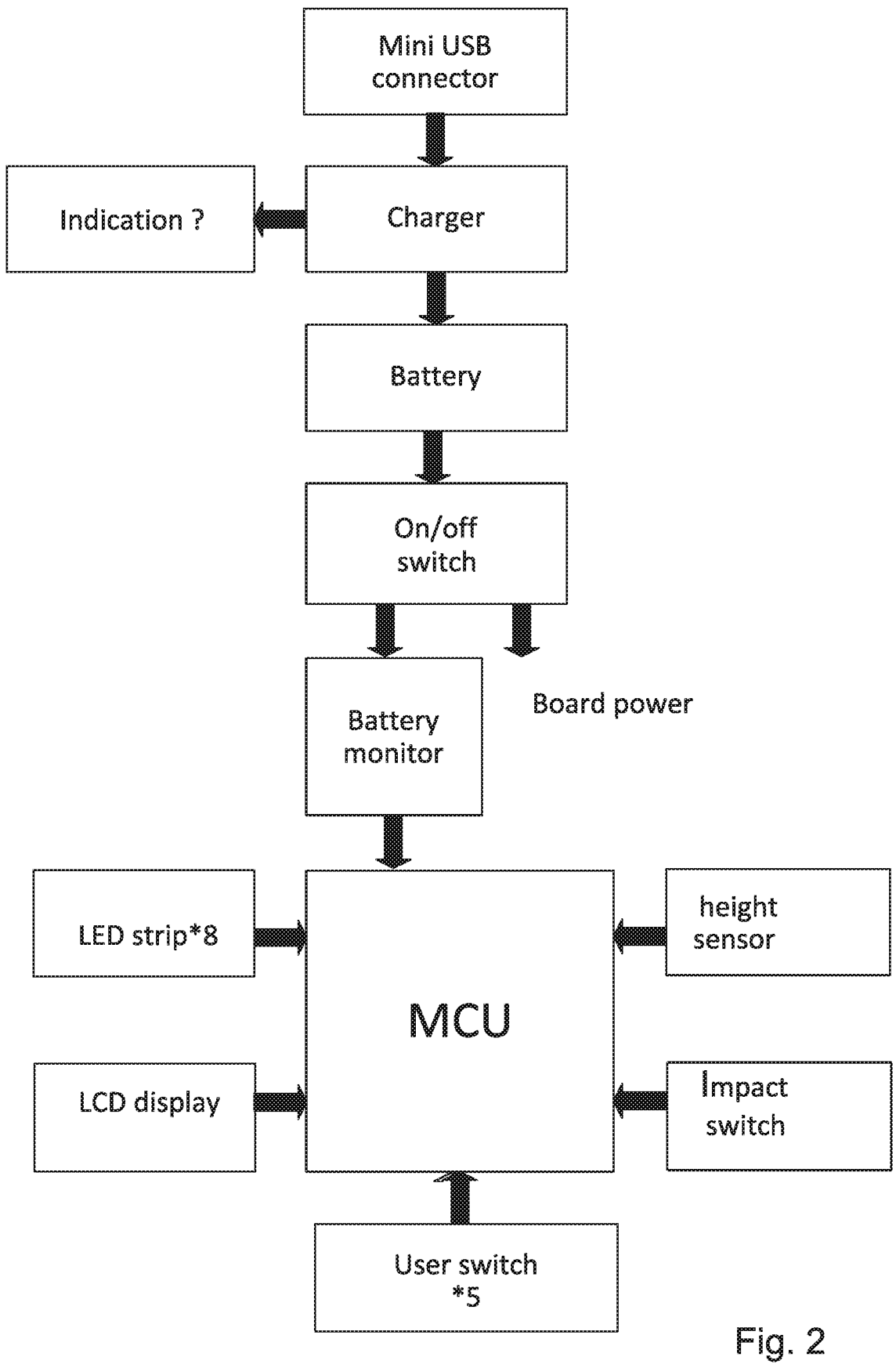
FIGS. 2-3, 7-8, are block diagrams useful in understanding certain embodiments which may for example be employed in conjunction with other embodiments illustrated herein.

An example block diagram for the board of the target is shown in FIG. 2; blocks provided may include some or all of the following: Rechargeable battery\Rechargeable battery connector; MCU control board activity; Impact sensor/tact switch (e.g. as shown in FIG. 1); Display e.g. LCD; Height sensor/altimeter; User-operated switch\buttons; LED strips or other output devices; and On off switch.

The term "tact switch" is intended to include any switch that only activates the relevant circuit when the user actually has contact with the switch e.g. by pressing the switch's button. As soon as the user terminates contact with the switch e.g. releases the button, the circuit is broken.

The term "impact switch" is intended to include any switch which is firmly mounted upon a device and senses shock thereto or vibration thereof.

The target typically includes elements operative to measure trainee response during training.

The target typically comprises some or all of: a switch to identify a hit (trainee-target impact or blow), height sensor, LED, LCD and control buttons.

FIG. 4 illustrates characteristics of an example mode of operation ("single strike mode"), all or any suitable subset of which may be provided.

FIG. 5 illustrates characteristics of an example mode of operation ("fake strike mode"), all or any suitable subset of which may be provided. In this mode, typically, the trainee is expected to refrain from taking any action.

FIG. 6a illustrates characteristics of an example mode of operation ("multiple strike mode"), all or any suitable subset of which may be provided.

Any suitable method may be employed to measure altitude in certain/all mode/s. For example, as shown in FIG. 6b, the altitude measurement method may include some or all of the following steps:

Step1: Enabling the altitude sensor.
Step2: Start counting time.
Step3: system operational flow interrupted by an event e.g. by a sensor.
Step4: Stop counting.
Step5: Convert the counted time to height result.
Or:
Step1: Enabling the altitude sensor. The system waits for digital returned result.
Step2: Returned result is converted to height.

According to certain embodiments, the system may detect user strikes during single strike (FIG. 4) and multiple strike (FIG. 6a) modes. The system may for example use an impact switch or accelerometer for strikes detection. The system may enable an impact switch or accelerometer "interrupt" during single strike and multiple strike modes.

The system may configure the control module for the LED/s of FIG. 3 in any suitable manner. For example:
Left\right pad side with Green LED and the opposite pad side with white LED.
Both pad sides with green LED.
Left\right pad side with 'Other' green LED and the opposite pad side with white LED.
Both pad sides with 'Other' green LED.
Both pad sides with Purple LED.

The system may configure the display module for the LCD/s of FIG. 3 e.g. using an SPI driver. The system may use commands protocol to control changes on screen.

The display may include some or all of the following:
Battery status; Current mode; Total training time; Multiple strike mode time; Response time after each strike during single strike mode.

The system may configure a time module, and may enable the timer to start and display total training time.

A buttons interrupt functionality may be provided. The system may configure a button interrupt module. The system may be interrupted by button clicks.

Each button "interrupt" typically causes the system to switch between the different modes e.g.:
Right green arrow button—right single strike mode.
Left green arrow button—left single strike mode.
Right 'other' green arrow button—right fake strike mode.
Left 'other' green arrow button—left fake strike mode.
Purple button—multiple strikes mode.

The system may support a separate calibration functionality e.g. for definition of a zero height or other set-up parameters.

Figure 7:
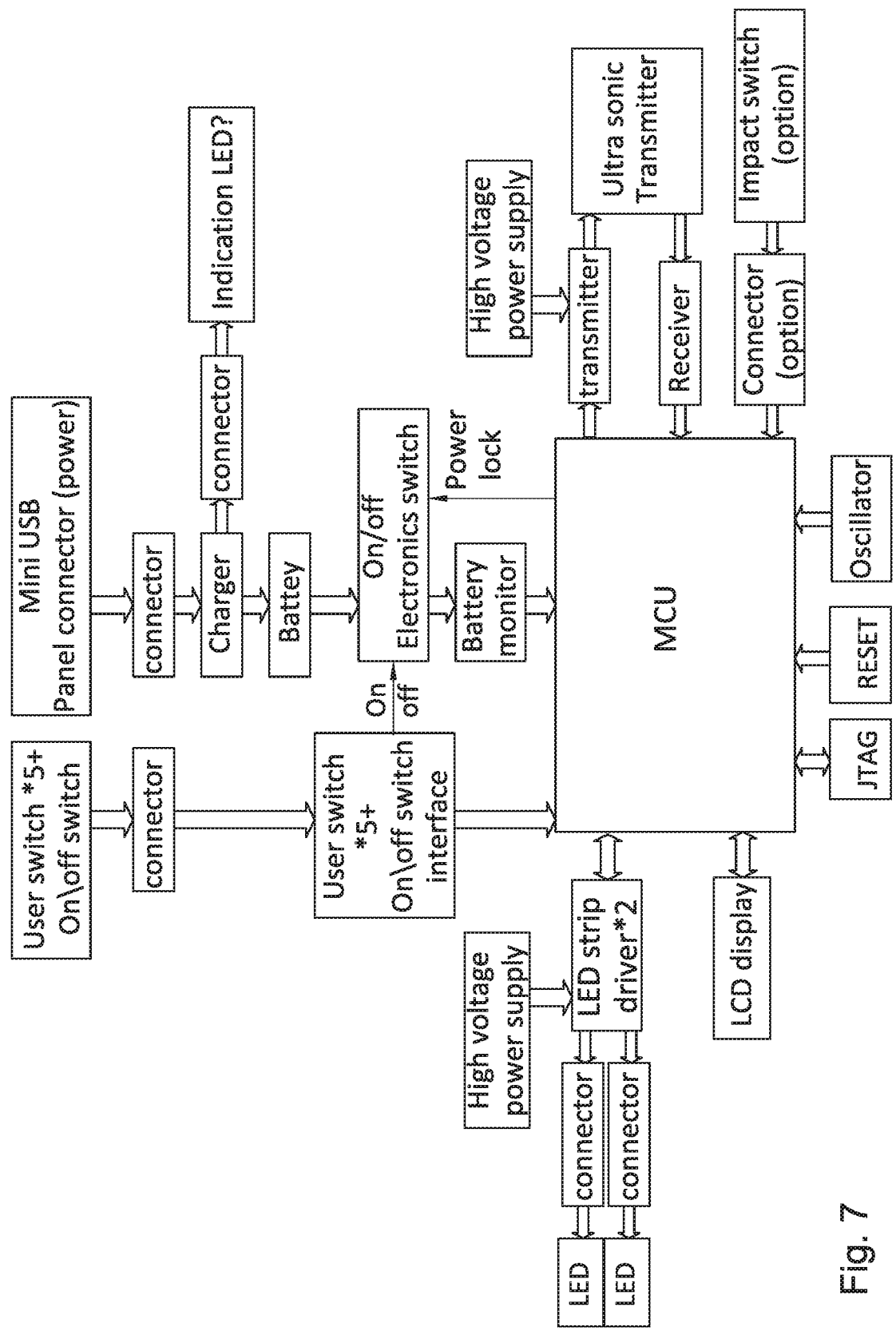

In FIG. 7, typically, the components other than the LEDs and connectors are provided on board/s and the on-board components interface via the connectors with the LEDs. Optionally, an accelerometer (not shown) may interface with the MCU.

Example: Some or all of the following specification details which are not intended to be limiting, may be provided, for an exemplary embodiment:
MCU (external Accelerometer)
Pin out:
5 GPIO for user switch ("interrupt" capability).
1 GPIO for power self-lock.
7 SPI (MOSI, MISO, CLOCK) and 3 CS (LCD, 2 LEE drivers, Accelerometer)
2 GPIO for ultrasonic.
1 ANALOG for battery monitoring.
2 ANALOG for internal power.
2 spare.
Total: 20 pin; Sub division: 1 SPI channel. 3 Analog. 16 GPIO.
Option 1: part number: STM8L052C6T6 by ST include 32 k flash, 2 k, Or (Option 2), part number: STM32F042K6T6 (Cortex®-M0) by ST include 32 k flash, 2 k RAM Or (Option 3): MMA959L by Freescale includes 14 k flash, include factory flash and MCU core cold fire v1.
A GPIO expander (example PCA9554BPWJ By NXP 0.65$/1000) and an external Accelerometer may be provided. One suitable Accelerometer for certain use cases is Part number: LIS2DH by ST Capable scale of ±2 g, ±4 g, ±8 g, ±16 g; Band width: 1 to 5.3 khz.

The LCD display may for example have a Interface SPI, Voltage 3-3.6V and suitable Mechanical interface e.g. header and screw (connection to the PCB).

The LED strip driver may include any suitable number of LEDs and an Interface SPI. Suitable battery size/capacity, charger, supply voltage for LED driver may be provided accordingly.

Any suitable number of user switches (say 5) may be provided; which might yield a total of 10 wires, 2 for each switch, or the total number may be reduced, say to 6. A normally open switch (disconnect if not open) may be employed.

A power on/off switch, e.g. a normally open switch (disconnect if not open—2 wire switch) may activate an on board electronics switch that powers up the MCU. The MCU may lock the electronics switch.

The unit may be powered off by depressing the on/off, or not pressing any button for, say, 10 minutes. The user and on off switches may be connected thru the same connector.

Battery monitoring may be provided so as to sample battery level for user indication. If no electronic switch is present in the design battery, monitoring may be enabled or disabled by the MCU.

Ultrasonic transmitter Activation may occur, say, by sending 5-10 pulses at 40 kHz and measure the time that the echo returns. An example of a suitable Part number is: MCUST10P40B07RO by MULTICOMP. It is appreciated that all commercially available parts mentioned herein are suitable for particular use cases and are not intended to be limiting.

The embodiment comprises a target e.g. paddle that comprises several elements operative to measure response during training.

The following training modes may be provided:
Single training mode
Fake training mode
Multiple training mode
The system gives an indication about the current mode by turning on LEDs.

The system collects parameters from the peripherals, calculates the parameters, and displays it on the LCD. The target may comprise some or all of: an accelerometer to identify a hit, height sensor, LED, LCD and control buttons.

Figure 19A:
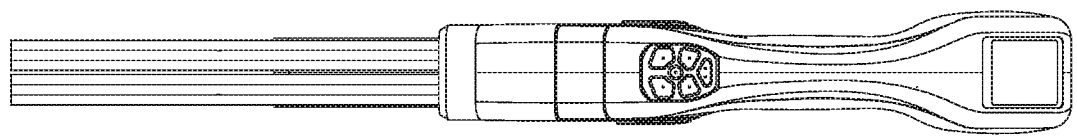
FIGS. 19a-19d are generally self-explanatory views of a target constructed and operative in accordance with an alternative embodiment of the present invention; it is appreciated that the target may have some or all of the characteristics illustrated, optionally in combination with some or all of the characteristics of the embodiment of FIG. 1.
Figure 19B:
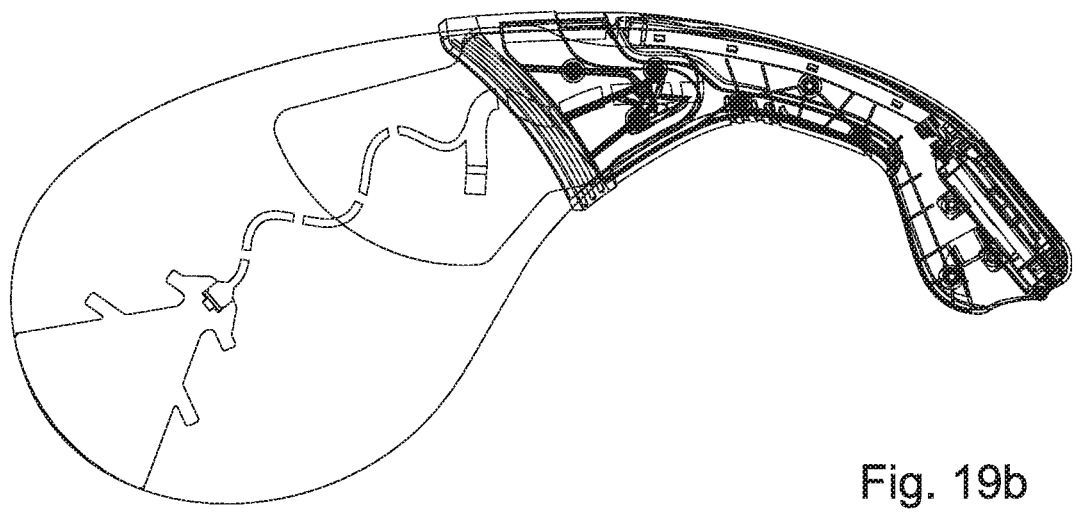
Figure 19C:
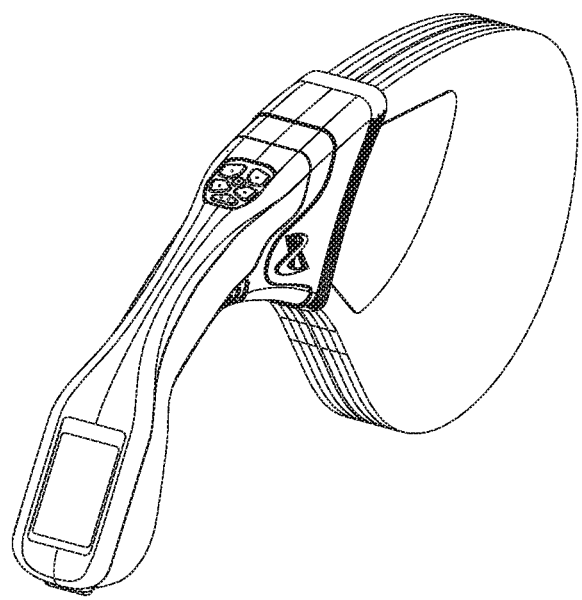
Figure 19D:
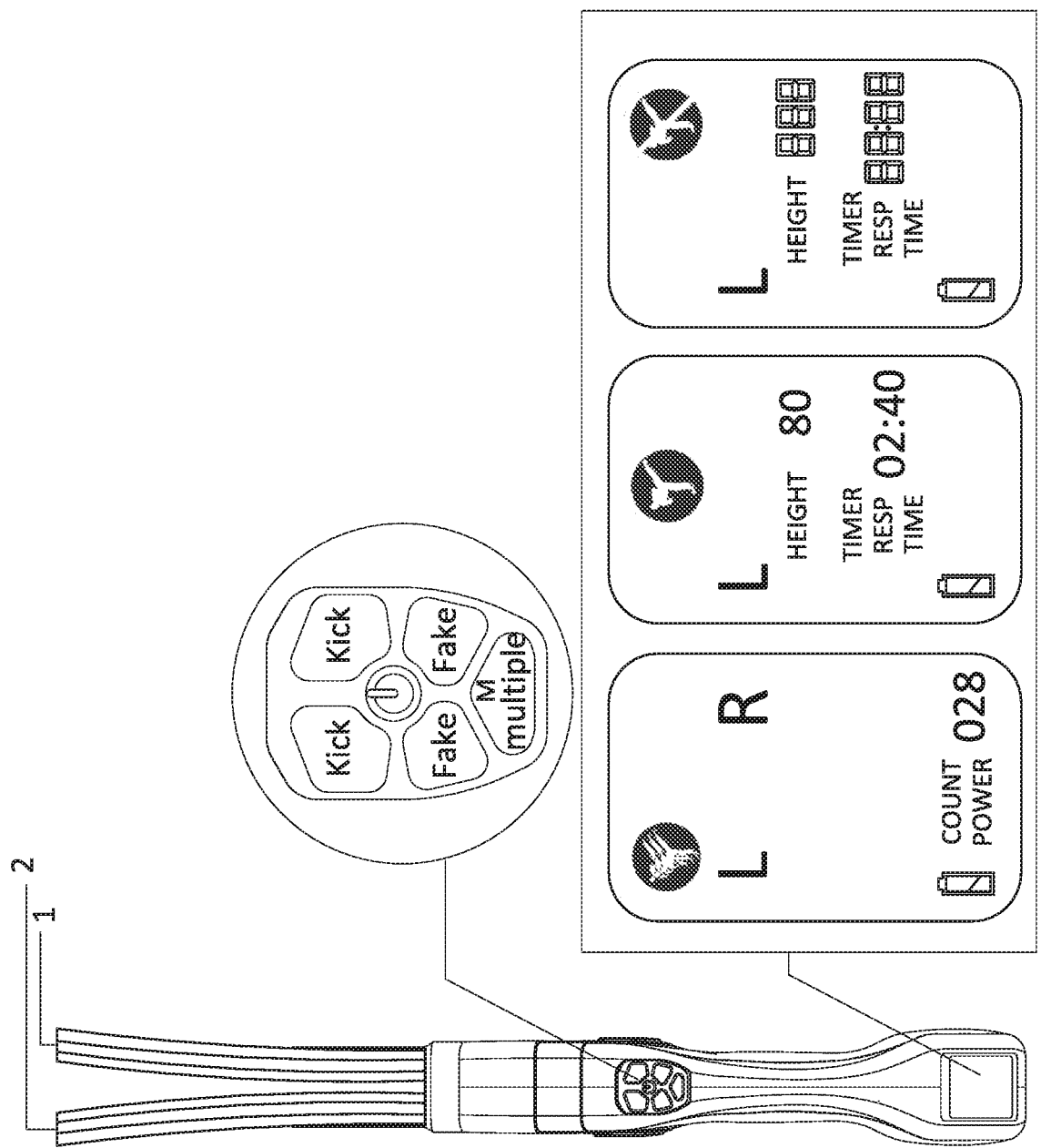

It is appreciated that different displays may be provided e.g. to the trainer, depending on the current mode, as shown for example in FIG. 19*d*.

Figure 8:
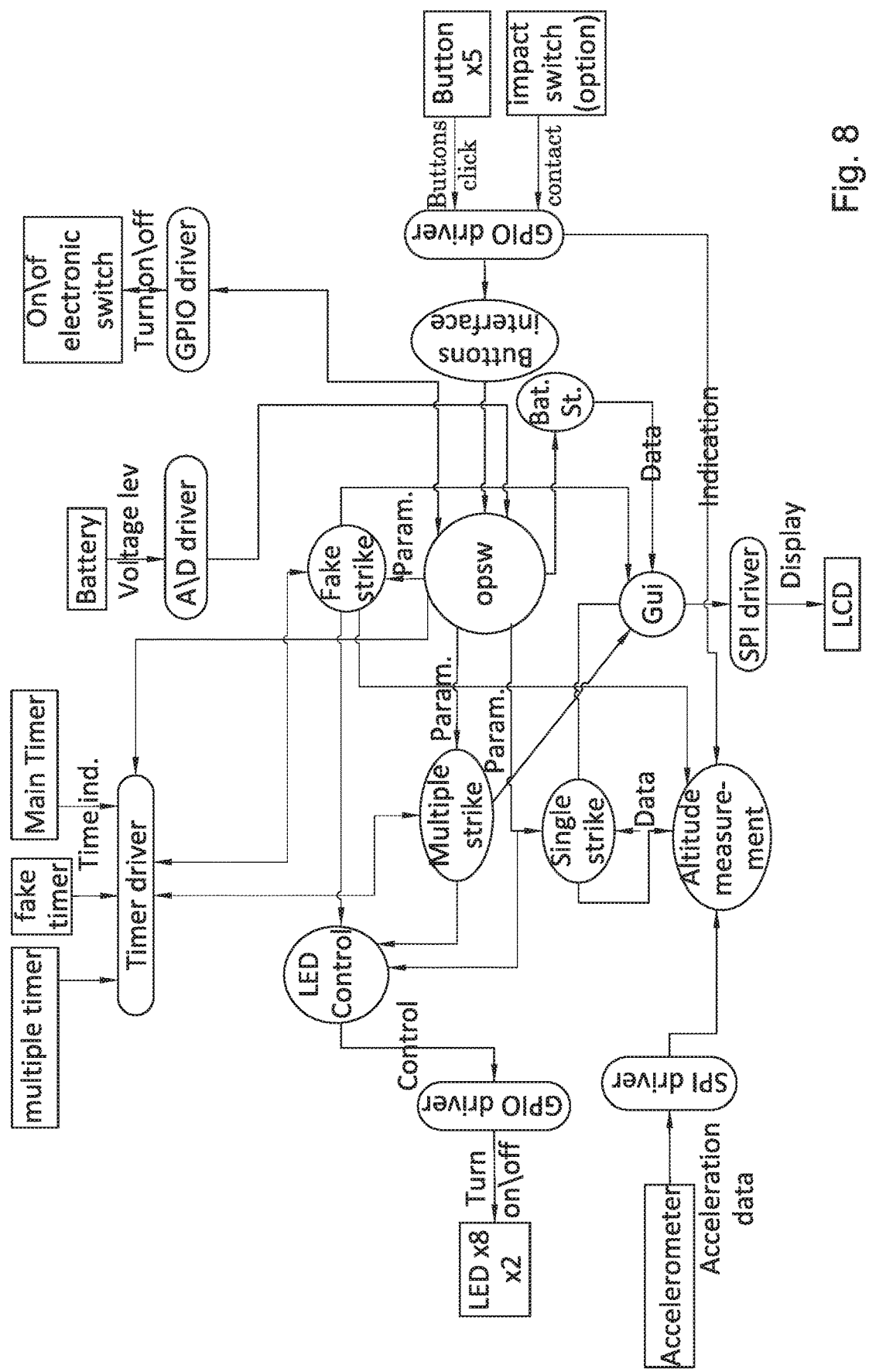

Functional Modules in FIG. 8 may include some or all of the following:

An optional ultrasonic module (not shown), providing ultrasonic data to the GIPO driver.

Buttons interface module of FIG. 8 is operative for button interrupts and activating the strike selection module e.g. responsively.

The OPSW module of FIG. 8 is operative for activating one of the main modules (fake, single and multiple strike); the OPSW typically gets indication from the button interface about the beginning of the training, and/or gets indication about the on/off switch, and, e.g. responsively, initiates the timer of the entire system.

The module displays the Battery Status on the LCD.

The OPSW checks if 10 minutes pass without pressing any button, and turns off the system by activating the on\off electronic switch.

Figure 9:
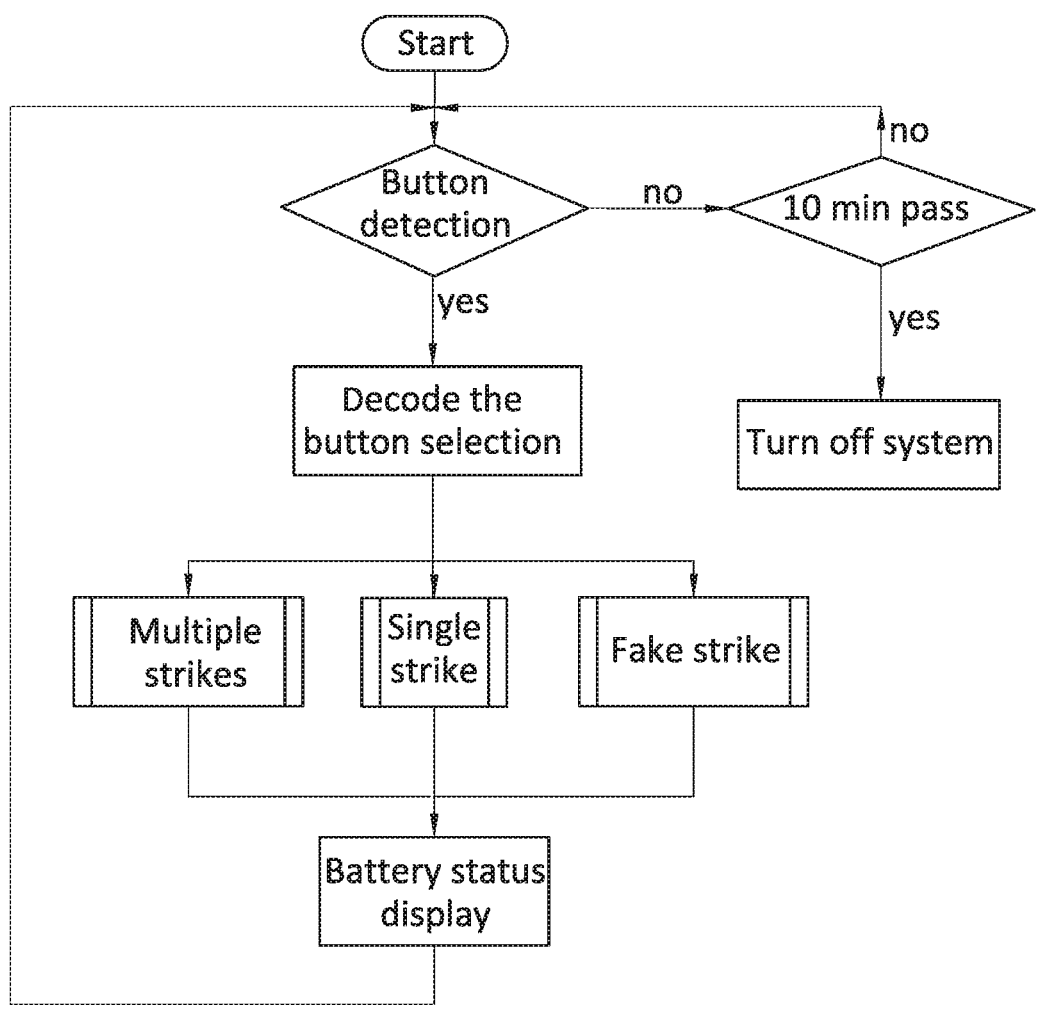
FIGS. 9-10, 11a-11b, 12-14, 15a-15b, 17a-17c are simplified flowchart illustrations of methods which may for example be employed in conjunction with other embodiments illustrated herein. Each method may for example include some or all of the illustrated operations, suitably ordered e.g. as shown.

FIG. 9 is a simplified flowchart illustration of an example method of operation of the system, including selection of one of various training modes (e.g. some or all of those shown and described herein or any other, depending on the use-case, sport or training goal, etc.) typically responsive to a trainer's (or system's) or even trainee's selection of a mode, e.g. using a suitable input device such as but not limited to an array of buttons one per mode, e.g. as shown in FIGS. 19*a*, 19*c* and 19*d*.

Figure 10:
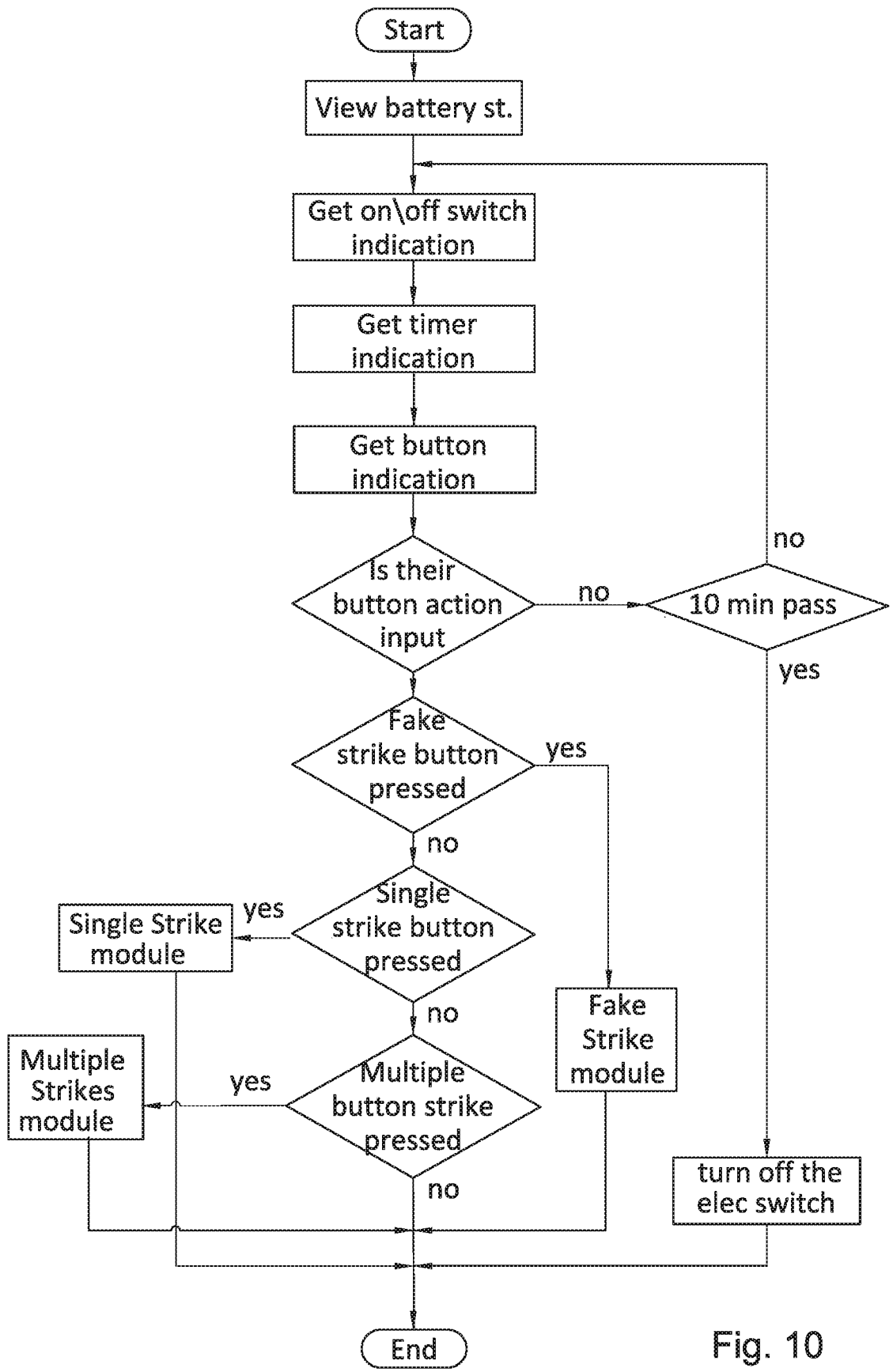

According to certain embodiments, an open pluggable specification workflow (OPSW module) is employed so as to standardize the design and development of digital signage devices and/or pluggable media players. FIG. 10 is an example flow chart for an OPSW module; some or all of the illustrated operations—in this drawing and others—may be provided, suitably ordered e.g. as shown.

Typically, the multiple strike module is operative for multiple strike training. The module input is indicated by clicking the multiple button, and checks whether the button was not pressed for more than 2 sec and terminates the module, if it was not pressed, then it turns on a timer that gets updates online, and increases 15 sec by pressing the multiple button multiple times.

After counting 2 sec after pressing the multiple button, the module turns on the LED module and the timer begins counting. The module also activates a counter that counts the sum of strikes that has been detected. In the last 10 sec of the first training, the module turns on a blinking LED, and the module sends all information to the LCD display. Blinking, or any other indication, may be provided to warn that a particular time-window (e.g. mode) is about to terminate.

Figure 11A:
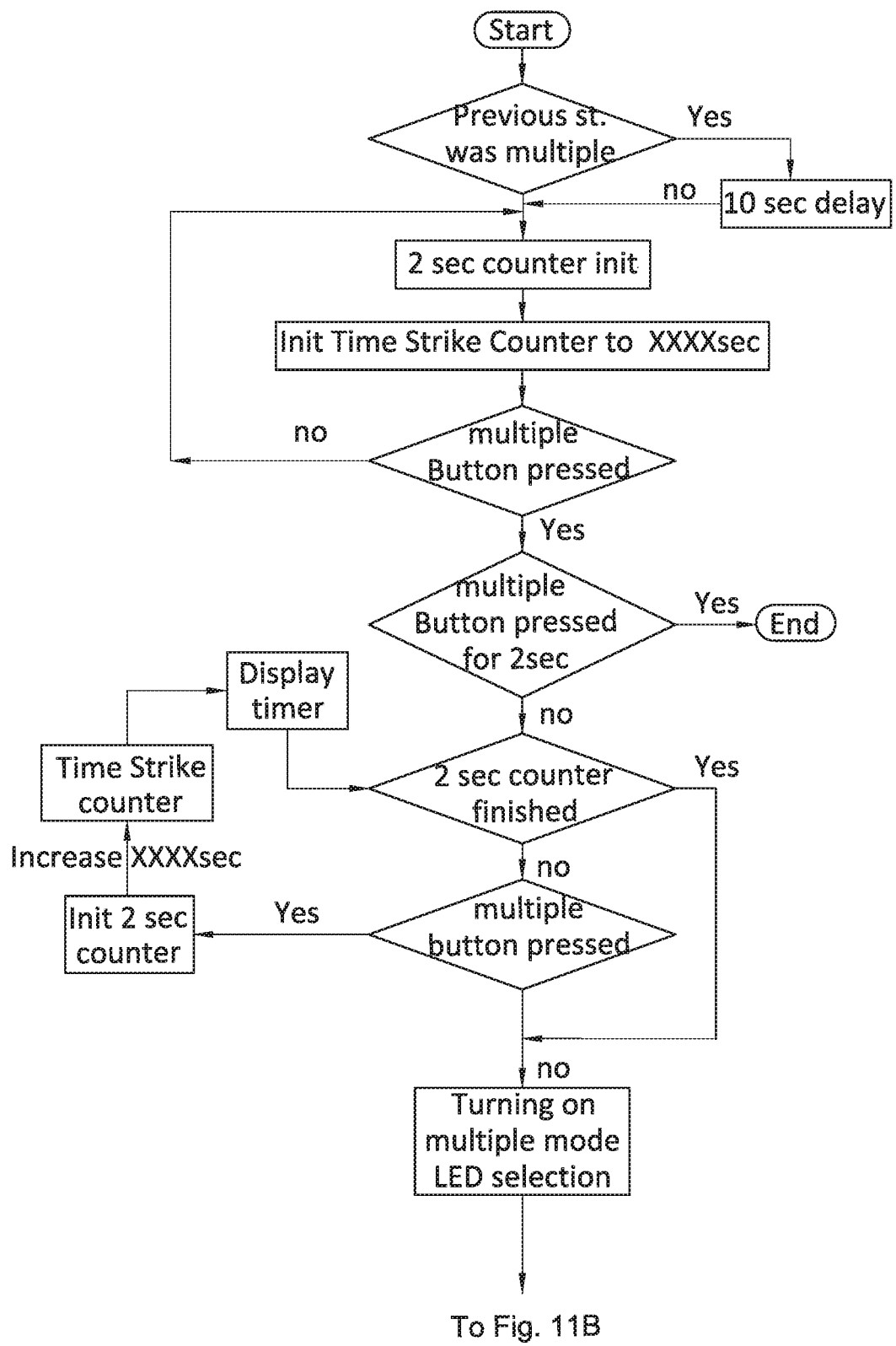
Figure 11B:
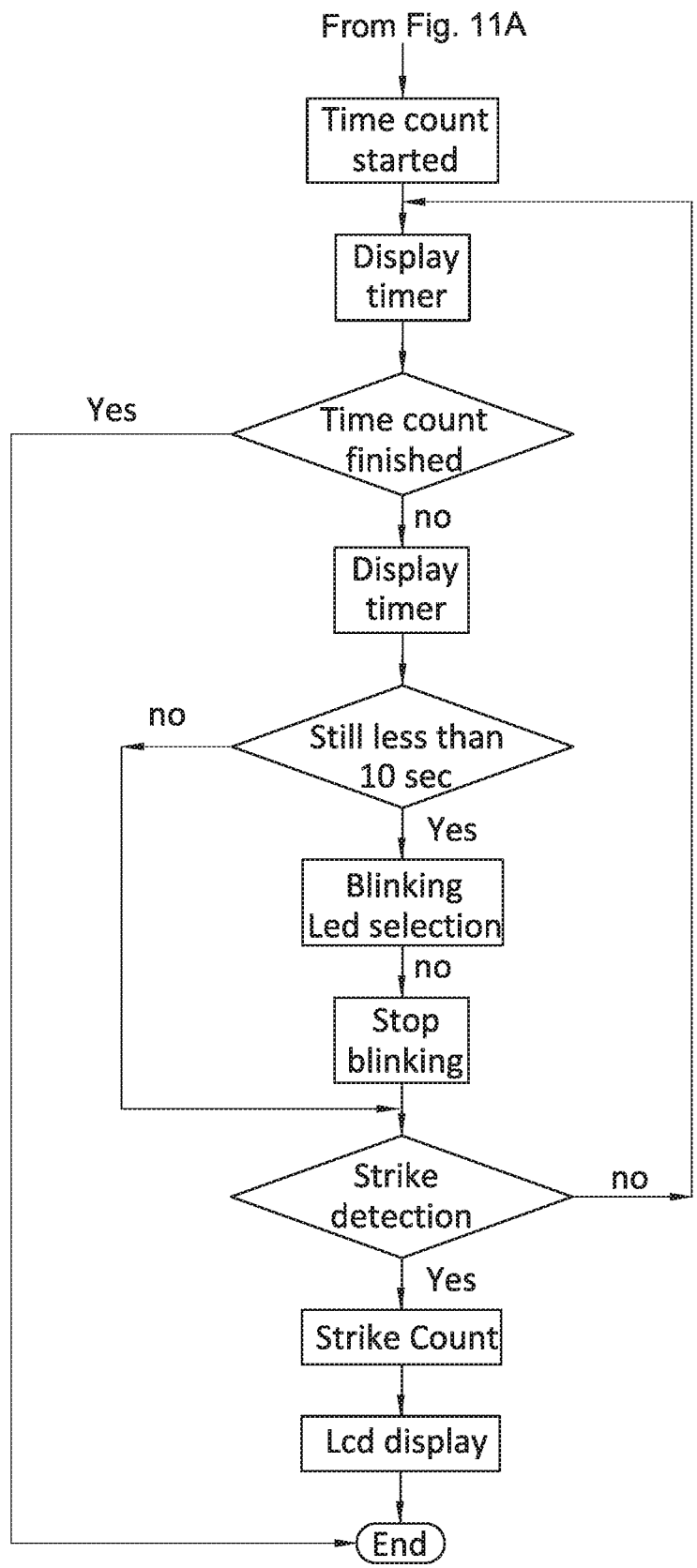

FIGS. 11*a*-11*b*, taken together, form a simplified flowchart illustration of operations, some or all of which may be performed by the multiple-strike module, in any suitable order e.g. as shown. According to certain embodiments, the "previous strike was multiple?" and "10 sec delay" blocks may be replaced by a "reset previous values" block.

It is appreciated that parameters such as "10", here and elsewhere, are of course merely exemplary and may be replaced by other suitable values as appropriate for a given use-case.

The single strike module is typically operative for single strike training. The module's input is indicated by clicking the single button. It turns on green\white LEDs, and also turns on a timer that counts the time of the training, and waits for 3 sec to get strike detection.

After getting the strike detection, the module gets indication about the altitude of the strike, and the module sends all information to the LCD display.

Figure 12:
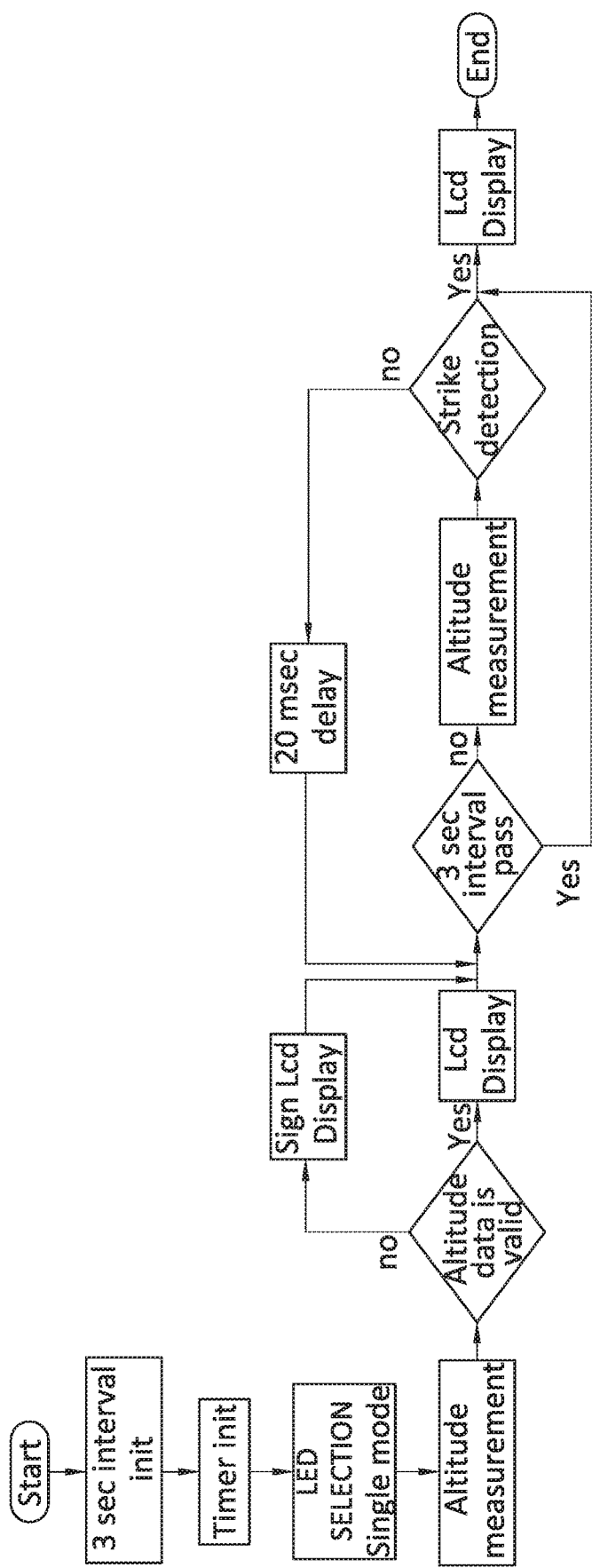

FIG. 12 is a simplified flowchart illustration of operations, some or all of which may be performed by the single-strike module, in any suitable order e.g. as shown.

Typically, the Fake strike module is operative for fake strike training, the module's input is an indication by clicking the fake button, it turns on yellow\white LEDs for 500 msec, delay the system for 500 msec and turns on a LED selection.

The module displays the system status on the LCD.

Figure 13:
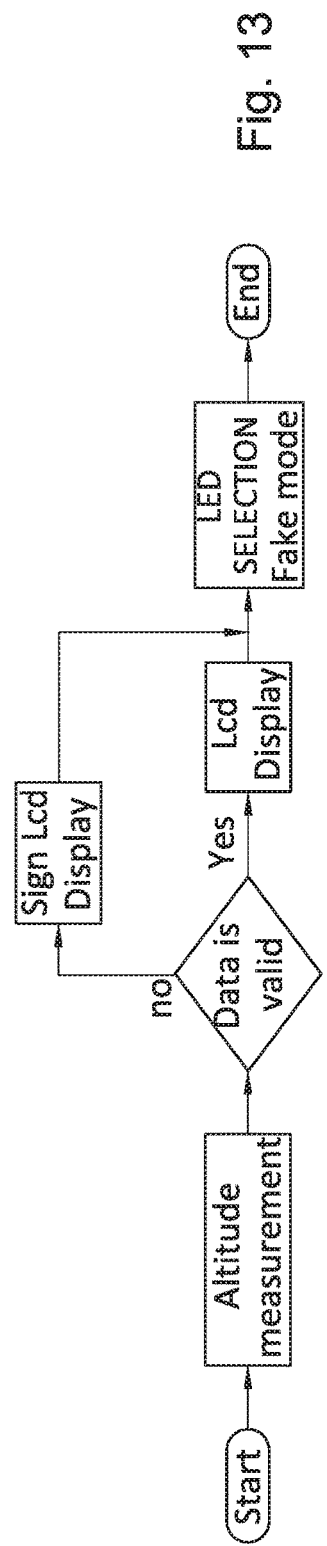

FIG. 13 is a simplified flowchart illustration of operations, some or all of which may be performed by the fake-strike module, in any suitable order e.g. as shown. The Control Module (FIG. 8) for the LED/s of FIG. 7 is operative for turning the LEDs of the heater, respectively to the system mode training.

The module may provide indicators of a plurality of selectable modes such as fake, single, multiple and blinking modes.

Figure 14:
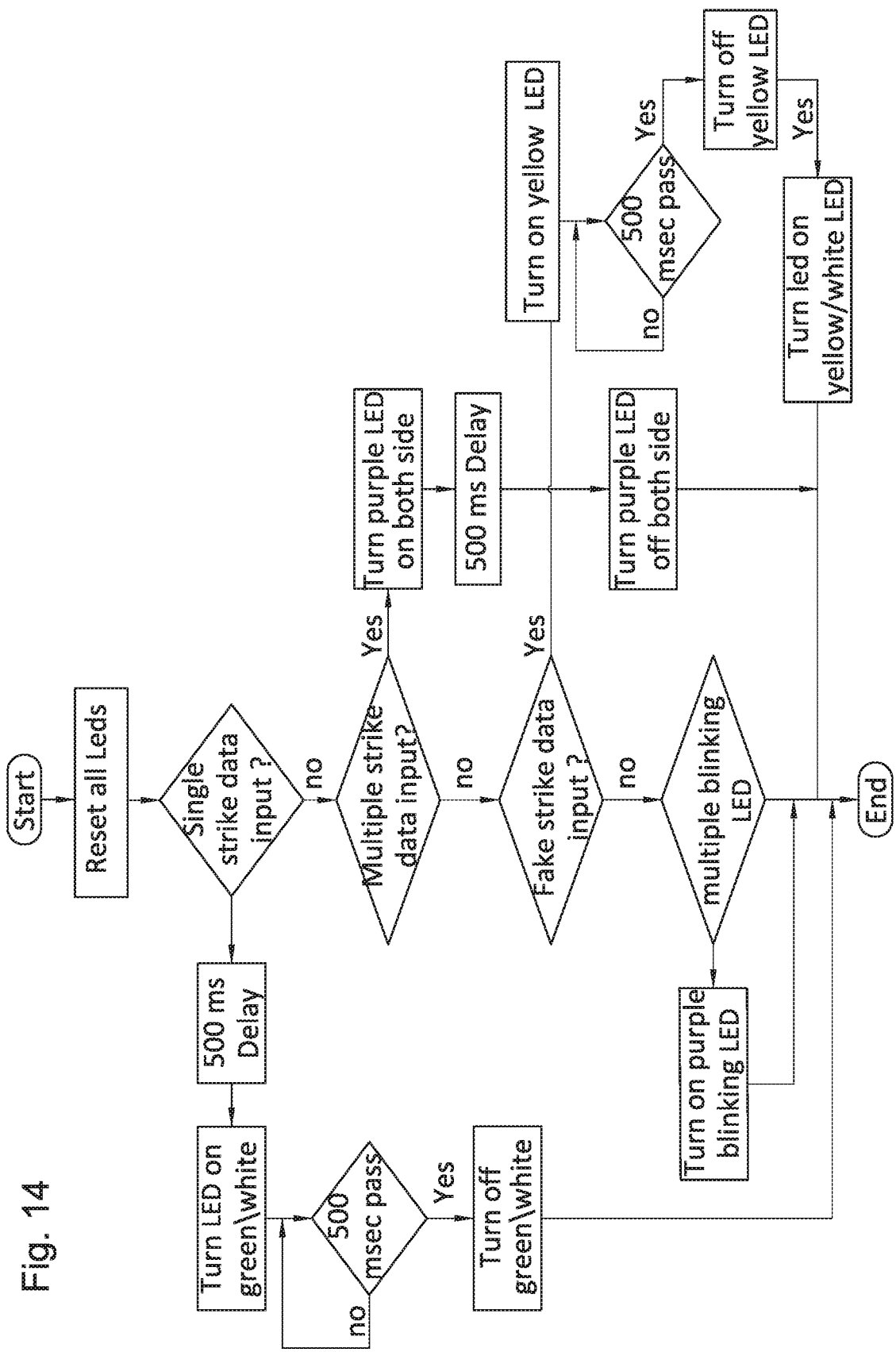

FIG. 14 is a simplified flowchart illustration of operations, some or all of which may be performed by the LED control module, in any suitable order e.g. as shown. The Battery Status module is operative to display the battery status.

Figure 15A:
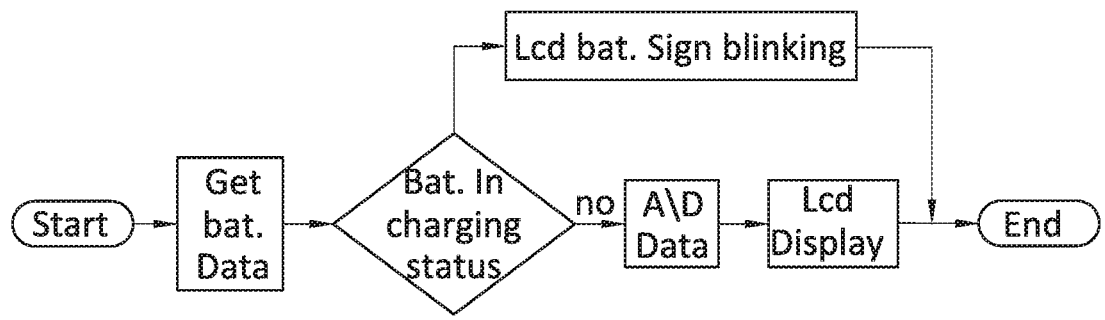

FIG. 15*a* is an example flowchart for a battery status module.

Figure 18:
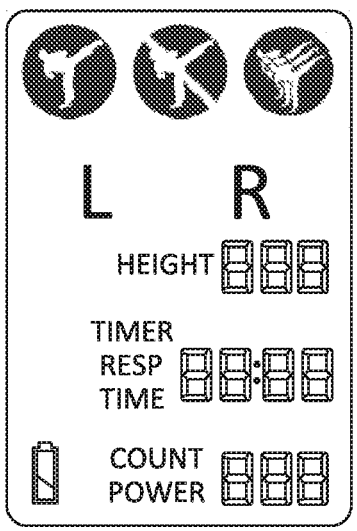

An LCD Display Module (FIG. 7) may be operative for sending commands to the LCD to display the values that systems compute e.g. regarding the battery status and mode of the system. An example display is shown in FIG. 18. As shown, LEDs are provided for each mode (e.g. single, fake and multiple strike modes respectively, from left to right in the top row in the illustrated embodiment—if the LED is on/off this may indicate to the trainee, to whom the panel is visible, that the corresponding mode is/is not currently in effect). Paddle height relative to ground and battery status may be displayed. Response time may be displayed and may represent different time-intervals for different modules; e.g.:

for single-strike mode: the time that elapsed from when the mode LED illuminated until when the paddle was contacted by the trainee; and for multiple-strike mode: the amount of time remaining until this mode is terminated and another mode comes into effect.

The "count power" data may also represent different data for different modules e.g. how many times the paddle was struck by a trainee in multiple-strike mode; and how hard the paddle was struck by a trainee in single-strike mode. Trainee impact with target surfaces disposed to trainee's right and left respectively (or with portions of a single surface disposed to trainee's right and left respectively), may be separately recorded and tagged "right" and "left" respectively in the computer memory. Records may be time-stamped as may be indications of which modes were presented to the trainee, thereby to obtain data allowing aspects of trainee's actual behavior to be compared to the required aspects of behavior mandated by various modes. For example, at 18:05 trainee should have kicked the right side of the target several times; instead he failed to kick at all; or perhaps the left side of the target was kicked but only once.

Use of the display of FIG. 18 (say) may be as follows: initially, other than battery status, all values are displayed as 0. The trainer (also termed herein "instructor", typically human or, alternatively, via software) typically chooses a mode and this is shown to the trainee e.g. one of the 3 LEDs lights up if 3 selectable modes are provided as in the illustrated embodiment. The trainer also chooses a lateral side e.g. right or left in which case the R or L LEDs may indicate this choice to the trainee. The trainee then does his best to kick the left or right sides of the target exactly once, as soon as possible after the trainer chooses "single kick mode" and left/right icon/LED respectively, or to kick the left or right sides of the target as often as possible for as long as the trainer has chosen the "multiple kick mode" icon, with left/right icon respectively, and is displayed or lit; or to refrain from kicking if the trainer chooses "fake kick mode" and, perhaps, one of the left/right icon/LEDs as well.

Of course, many variations of the display of FIG. 18 are possible. For example, rather than separately selecting R/L and one of n modes 1, . . . n, the trainer may select one of 2n modes namely mode 1—right side of target; mode 1—left; mode 2—right side of target; mode 2—left; etc. Any number of icons/LEDs or other display elements may be used to show the trainee which mode is current such as n such (one icon/LED per mode) or just 1 display element e.g. screen having n different states. For example, a plurality of "mode" indicators may be arranged in a circle e.g. surrounding the target's on-off button.

Figure 15B:
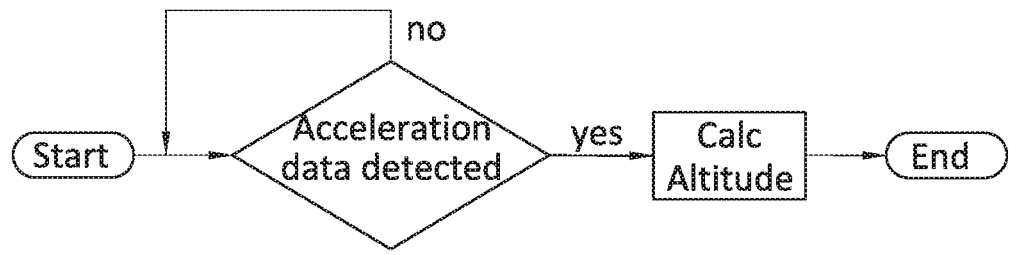

The altitude measurement module of FIG. 8 is operative for collecting acceleration data from the accelerometer of FIG. 7 and computing the altitude of the strike detection and sending back the data to the single strike mode training e.g. as shown in the Flow Chart illustration of FIG. 15b. The GPIO driver of FIG. 8 is typically operative for controlling some peripherals (digital output), and as reference (input indicators) to valves and switches state.

Figure 16A:
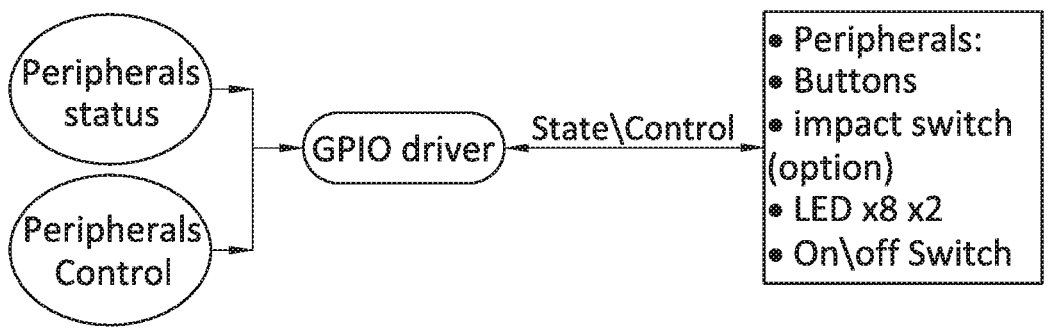
FIGS. 16a-16c and 18 are diagrams and illustrations useful in understanding certain embodiments which may for example be employed in conjunction with other embodiments illustrated herein.

The peripherals controlled by pins may include some or all of the following:
Buttons; impact switch; (LED×8×2; on\off switch and may be operative e.g. as shown in the flow chart of FIG. 16a.

Figure 16B:
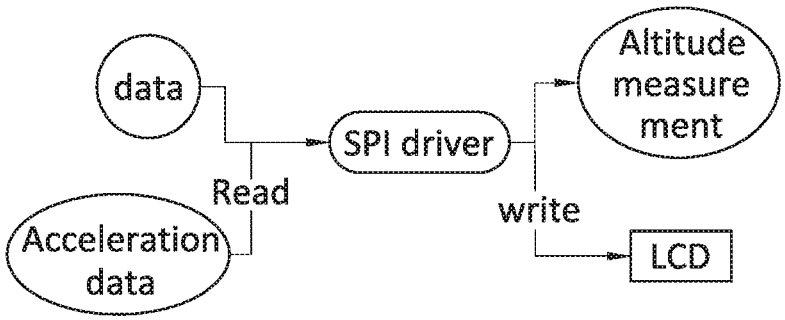

The SPI driver of FIG. 8 may be operative for displaying data on the LCD, and to read information from the accelerometer e.g. as shown in the flow chart of FIG. 16b.

Figure 16C:
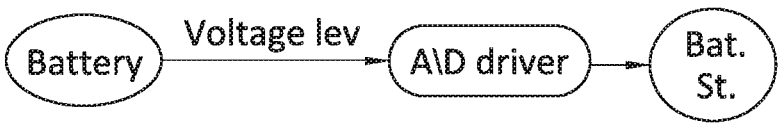

The A\D driver of FIG. 8 may be operative for interfacing the PC with the MCU e.g. as shown in the flow chart of FIG. 16c.

FIG. 7 is a hardware design diagram of example TTE (Taekwondo training equipment) main board, according to certain embodiments; more generally there are of course many uses besides Taekwondo, besides martial arts and besides sports, e.g. for remedial or educational work. The microcontroller unit—MCU—may, for example, be based on part number MKL25Z64VLH4 by ST, having an 8 bit core, Oscillator 16 MHz, and 32 k flash.

The external accelerometer of FIG. 7 may for example comprise Part number LIS2DH by ST, having the ability to measure up to 5 KHz and Communication SPI.

An LCD connector may be provided e.g. with a 3 wire interface (SPI) and a backlight LED which is always on.

The Switch interface of FIG. 7 may comprise a switch with common GND and one on-off switch for power.

The Battery charger of FIG. 7 may be based on the MCP73832 BY MICROCHIP with the ability to change charge current.

A DC-DC convertor may provide: 10V and 2.5V for ultrasonic driver; 5V for RGB LED.

The RGB LED driver of FIG. 7 may comprise 2 RGB LED drivers with an IIC interface.

An inlet switch may be provided to support self-lock for power; a high side switch may be placed on the power line.

An Ultrasonic driver may include a transmitter (e.g. US transmitter in FIG. 7) and receiver driver for ultrasonics sensor; this may be used e.g. for measuring height of the target vis a vis a "zero" height at a given time e.g. when the trainee impacts the target.

Redundancy, such as one or more of: connectors for ultrasonic sensor, spare accelerometer, spare impact switch may be provided.

An example embodiment comprises a standard like target that comprises several elements operative to measure response during training.

An example embodiment comprises, typically, some or all of the following modes: Single training mode; Fake training mode; and Multiple training mode.

The system typically gives a trainee and/or trainer sensible indication of the current mode e.g. by turning on suitable LEDs. Typically, the system collects parameters from the peripherals, computes the parameters and displays it on the LCD. The target may include some or all of an accelerometer to identify a hit, height sensor, LED, LCD and control buttons. The Buttons interface module of FIG. 8 is operative for "button interrupts" (e.g. events in which a button is activated) and activates the strike selection module.

Figure 17A:
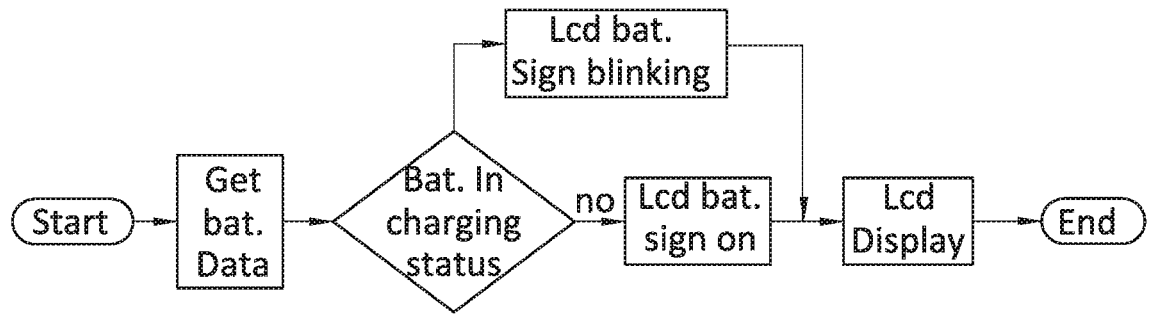

FIG. 17a is an alternative to the embodiment presented in FIG. 15a. As described above, the Functional Modules in FIG. 8 may include an ultrasonic module (not shown), providing ultrasonic data to the GIPO driver. The altitude measurement module of FIG. 8 is typically operative for collecting the Ultrasonic data from the Ultrasonic module and computing the altitude of the strike detection and sending back the data to the single strike mode training.

Figure 17B:
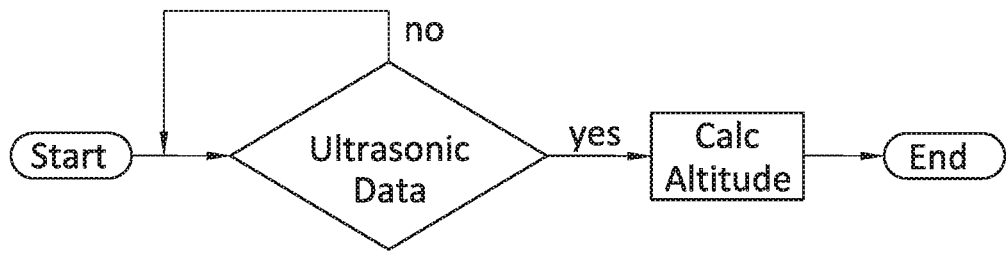

FIG. 17b is an alternative to the embodiment presented in FIG. 15b.

Typically, a Hardware Control module (e.g. as shown in FIG. 7) is operative to initiate hardware and send bits to the hardware, and return indications about failure.

Typically, a Strike Detection module (e.g. as shown in FIG. 12) is operative for collecting the acceleration data from the accelerometer and decode whether any impact took place.

Figure 17C:
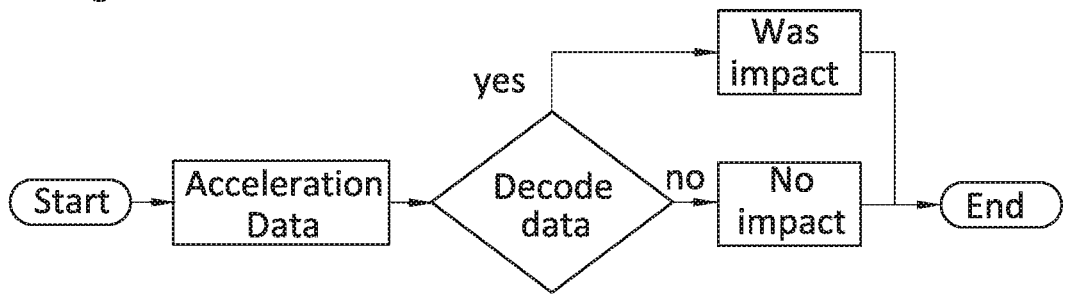

FIG. 17c is an alternative to the embodiment presented in FIG. 15c.

It is appreciated that methods represented by flow charts may include any suitable subset of the steps illustrated. Tables may include any suitable subset of the table-cells/rows/columns illustrated. Diagrams may include any suitable subset of the modules/blocks illustrated.

It is thus appreciated that terminology such as "mandatory", "required", "need" and "must" refer to implementation choices made within the context of a particular implementation or application described herewithin for clarity and are not intended to be limiting since in an alternative implantation, the same elements might be defined as not mandatory and not required or might even be eliminated altogether.

It is appreciated that software components of the present invention including programs and data may, if desired, be implemented in ROM (read only memory) form including CD-ROMs, EPROMs and EEPROMs, or may be stored in any other suitable typically non-transitory computer-readable medium such as but not limited to disks of various kinds, cards of various kinds and RAMs. Components described herein as software may, alternatively, be implemented wholly or partly in hardware and/or firmware, if desired, using conventional techniques, and vice-versa. Each module or component may be centralized in a single location or distributed over several locations.

Included in the scope of the present disclosure, inter alia, are electromagnetic signals in accordance with the description herein. These may carry computer-readable instructions for performing any or all of the operations of any of the methods shown and described herein, in any suitable order including simultaneous performance of suitable groups of operations as appropriate; machine-readable instructions for performing any or all of the operations of any of the methods shown and described herein, in any suitable order; program storage devices readable by machine, tangibly embodying a program of instructions executable by the machine to perform any or all of the operations of any of the methods shown and described herein, in any suitable order; a computer program product comprising a computer useable medium having computer readable program code, such as executable code, having embodied therein, and/or including computer readable program code for performing, any or all of the operations of any of the methods shown and described herein, in any suitable order; any technical effects brought about by any or all of the operations of any of the methods shown and described herein, when performed in any suitable order; any suitable apparatus or device or combination of such, programmed to perform, alone or in combination, any or all of the operations of any of the methods shown and described herein, in any suitable order; electronic devices each including at least one processor and/or cooperating input device and/or output device and operative to perform e.g. in software any operations shown and described herein; information storage devices or physical records, such as disks or hard drives, causing at least one computer or other device to be configured so as to carry out any or all of the operations of any of the methods shown and described herein, in any suitable order; at least one program pre-stored e.g. in memory or on an information network such as the Internet, before or after being downloaded, which embodies any or all of the operations of any of the methods shown and described herein, in any suitable order, and the method of uploading or downloading such, and a system including server/s and/or client/s for using such; at least one processor configured to perform any combination of the described operations or to execute any combination of the described modules; and hardware which performs any or all of the operations of any of the methods shown and described herein, in any suitable order, either alone or in conjunction with software. Any computer-readable or machine-readable media described herein is intended to include non-transitory computer- or machine-readable media.

Any computations or other forms of analysis described herein may be performed by a suitable computerized method. Any operation or functionality described herein may be wholly or partially computer-implemented e.g. by one or more processors. The invention shown and described herein may include (a) using a computerized method to identify a solution to any of the problems or for any of the objectives described herein, the solution optionally include at least one of a decision, an action, a product, a service or any other information described herein that impacts, in a positive manner, a problem or objectives described herein; and (b) outputting the solution.

The system may, if desired, be implemented as a web-based system employing software, computers, routers and telecommunications equipment as appropriate.

Any suitable deployment may be employed to provide functionalities e.g. software functionalities shown and described herein. For example, a server may store certain applications, for download to clients, which are executed at the client side, the server side serving only as a storehouse. Some or all functionalities e.g. software functionalities shown and described herein may be deployed in a cloud environment. Clients e.g. mobile communication devices such as smartphones may be operatively associated with, but external to, the cloud.

The scope of the present invention is not limited to structures and functions specifically described herein and is also intended to include devices which have the capacity to yield a structure, or perform a function, described herein, such that even though users of the device may not use the capacity, they are if they so desire able to modify the device to obtain the structure or function.

Features of the present invention, including operations, which are described in the context of separate embodiments may also be provided in combination in a single embodiment. For example, a system embodiment is intended to include a corresponding process embodiment and vice versa. Also, each system embodiment is intended to include a server-centered "view" or client centered "view", or "view" from any other node of the system, of the entire functionality of the system, computer-readable medium, apparatus, including only those functionalities performed at that server or client or node. Features may also be combined with features known in the art and particularly although not limited to those described in the Background section or in publications mentioned therein.

Conversely, features of the invention, including operations, which are described for brevity in the context of a single embodiment or in a certain order may be provided separately or in any suitable subcombination, including with features known in the art (particularly although not limited to those described in the Background section or in publications mentioned therein) or in a different order. "e.g." is used herein in the sense of a specific example which is not intended to be limiting. Each method may comprise some or all of the operations illustrated or described, suitably ordered e.g. as illustrated or described herein.

Devices, apparatus or systems shown coupled in any of the drawings may in fact be integrated into a single platform in certain embodiments or may be coupled via any appropriate wired or wireless coupling such as but not limited to optical fiber, Ethernet, Wireless LAN, HomePNA, power line communication, cell phone, PDA, Blackberry GPRS, Satellite including GPS, or other mobile delivery. It is appreciated that in the description and drawings shown and described herein, functionalities described or illustrated as systems and sub-units thereof can also be provided as methods and operations therewithin, and functionalities described or illustrated as methods and operations therewithin can also be provided as systems and sub-units thereof. The scale used to illustrate various elements in the drawings is merely exemplary and/or appropriate for clarity of presentation and is not intended to be limiting.

The invention claimed is:

1. A martial arts training paddle comprising:
  (a) a handle and a strike target;
  (b) a trainer input interface positioned on said handle;
  (c) at least one indicator providing an indication sensible by a trainee and responsive to inputs from said trainer input interface; and
  (d) an altimeter.

2. A martial arts training paddle according to claim 1, comprising a display on said handle.

3. A martial arts training paddle according to claim 1, wherein said at least one indicator comprises at least one light.

4. A martial arts training paddle according to claim 1, comprising an accelerometer.

5. A martial arts training paddle according to claim 1, comprising a power source.

6. A martial arts training paddle comprising:
(a) a handle and a strike target;
(b) buttons positioned on said handle;
(c) at least one indicator providing an indication sensible by a trainee and responsive to inputs from said buttons; and
(d) an altimeter.

7. A martial arts training paddle according to claim 6, comprising a display on said handle.

8. A martial arts training paddle according to claim 6, wherein said at least one indicator comprises at least one light.

9. A martial arts training paddle according to claim 6, comprising an accelerometer.

10. A martial arts training paddle according to claim 6, comprising a power source.

11. A martial arts training paddle comprising:
(a) a handle;
(b) a strike target; and
(c) an altimeter.

12. A martial arts training paddle according to claim 11, comprising a display on said handle.

13. A martial arts training paddle according to claim 11, wherein said at least one indicator comprises at least one light.

14. A martial arts training paddle according to claim 11, comprising an accelerometer.

15. A martial arts training paddle according to claim 11, comprising a power source.

16. A martial arts training paddle according to claim 11, comprising buttons positioned on said handle.

* * * * *